(12) United States Patent
Jamiolkowski et al.

(10) Patent No.: US 9,181,427 B2
(45) Date of Patent: Nov. 10, 2015

(54) ABSORBABLE BIMODAL POLYMERIC BLEND COMPOSITIONS, PROCESSING METHODS, AND MEDICAL DEVICES

(71) Applicant: Ethicon, Inc., Somerville, NJ (US)

(72) Inventors: Dennis D. Jamiolkowski, Long Valley, NJ (US); Sasa Andjelic, Nanuet, NY (US); Brian M. Kelly, Ringoes, NJ (US); Christopher DeFelice, Springfield, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 14/533,274

(22) Filed: Nov. 5, 2014

(65) Prior Publication Data

US 2015/0159011 A1    Jun. 11, 2015

Related U.S. Application Data

(60) Provisional application No. 61/914,464, filed on Dec. 11, 2013.

(51) Int. Cl.

| | |
|---|---|
| *C08G 63/91* | (2006.01) |
| *C08L 67/04* | (2006.01) |
| *A61L 31/04* | (2006.01) |
| *A61L 31/14* | (2006.01) |
| *A61L 27/18* | (2006.01) |
| *A61L 29/06* | (2006.01) |
| *A61L 31/06* | (2006.01) |
| *A61B 17/064* | (2006.01) |
| *A61L 17/12* | (2006.01) |
| *C08G 63/664* | (2006.01) |
| *C08G 65/32* | (2006.01) |

(52) U.S. Cl.
CPC ............... *C08L 67/04* (2013.01); *A61B 17/064* (2013.01); *A61L 17/12* (2013.01); *A61L 27/18* (2013.01); *A61L 29/06* (2013.01); *A61L 31/041* (2013.01); *A61L 31/06* (2013.01); *A61L 31/148* (2013.01); *C08G 63/664* (2013.01); *C08L 2201/06* (2013.01); *C08L 2203/02* (2013.01); *C08L 2205/02* (2013.01)

(58) Field of Classification Search
CPC ................................ C08L 67/04; C08G 63/08
USPC ........................................................ 525/411
See application file for complete search history.

(56) References Cited

U.S. PATENT DOCUMENTS 4,646,741 A    3/1987    Smith
8,236,904 B2   8/2012    Andjelic et al.

*Primary Examiner* — Terressa Boykin
(74) *Attorney, Agent, or Firm* — E. Richard Skula

(57) ABSTRACT

Novel absorbable polymeric blends having bimodal molecular weight distribution are disclosed. The bimodal blends have a first component that is a polylactide polymer or a copolymer of lactide and glycolide having a bimodal molecular weight distribution, and a second component that is a poly(p-dioxanone) polymer of unimodal or bimodal molecular weight distribution. Alternately, the bimodal blends have a first component that is a polylactide polymer or a copolymer of lactide and glycolide having a unimodal molecular weight distribution, and a second component that is a poly(p-dioxanone) polymer of bimodal molecular weight distribution. The novel polymeric bimodal molecular weight blends provide medical devices having improved dimensional stability. Also disclosed are novel absorbable medical devices made from these novel bimodal polymer blends, as well as novel methods of manufacture.

23 Claims, 5 Drawing Sheets

ABSORBABLE BIMODAL POLYMERIC BLEND COMPOSITIONS, PROCESSING METHODS, AND MEDICAL DEVICES

FIELD OF THE INVENTION

The field of art to which this invention relates is absorbable polymers, in particular, absorbable bimodal molecular weight polymer blends useful for manufacturing medical devices.

BACKGROUND OF THE INVENTION

Absorbable polymers and medical devices made from such polymers are known in the art. Conventional absorbable polymers include polylactic acid, polylactide, poly(p-dioxanone), polyglycolic acid, polyglycolide, and copolymers of lactide, glycolide, p-dioxanone, trimethylene carbonate, ε-caprolactone, in various combinations, etc. The absorbable polymers are designed to have chemistry such that the polymers breakdown in vivo and are either metabolized or otherwise degraded, for example by hydrolysis, and excreted from the patient's body. The advantages of utilizing implantable medical devices made from absorbable polymers are numerous and include, for example, eliminating the need for additional surgeries to remove an implant after it serves its function. Ideally when a "temporary presence" of the implant is desired, support can be provided until the tissue heals.

Absorbable is meant to be a generic term, which may also include bioabsorbable, resorbable, bioresorbable, degradable or biodegradable. Likewise, absorption is meant to be a generic term, which may also include bioabsorption.

The absorbable polymers used to manufacture medical devices have been on occasion polymeric blends of absorbable polymers and copolymers engineered to provide specific characteristics and properties to the manufactured medical device, including absorption rates, mechanical properties, mechanical property loss rates post-implantation (e.g. breaking strength retention), and dimensional stability, etc.

There are many conventional processes used to manufacture medical devices from absorbable polymers and polymer blends. The processes include injection molding, solvent casting, extrusion, machining, cutting and various combinations and equivalents. A particularly useful and common manufacturing method is thermal forming using conventional injection molding processes. It is known in this art that manufacturing processes such as thermal injection molding may result in molded parts that have inferior properties, especially, for example, unacceptable dimensional stability, mechanical properties, and retention of mechanical properties with time post-implantation. There are a number of reasons for diminished dimensional stability. They include the presence of residual stresses induced during the manufacturing process. Another reason is if at least one of the polymeric components possesses too low a glass transition temperature, especially if the polymeric component does not easily crystallize after molding.

Therefore, there is a need in this art for novel absorbable polymer blends that can be used in thermal injection molding processes, and other conventional processes, to manufacture absorbable medical devices having superior mechanical properties such as stiffness and strength, superior mechanical property retention post-implantation, excellent absorption characteristics, manufacturability, and superior dimensional stability.

It is known when using thermal injection molding processes that process conditions and design elements that reduce shear stress during cavity filling will typically help to reduce flow-induced residual stress. Likewise, those conditions that promote sufficient packing and uniform mold cooling will also typically tend to reduce thermally-induced residual stress. It is often very difficult, if not nearly impossible to completely eliminate residual stress in injection molded parts. Approaches that have been employed to prevent warpage in parts having residual stress include: (1) attempting to crystallize the part while still in the mold to increase the mechanical rigidity to resist distortion; and, (2) employing resins having a high glass transition temperature ($T_g$).

This later case describes the situation wherein chain mobility is only reached at much higher temperatures, thus protecting the part at the moderate temperatures that the part might be expected to endure during ethylene oxide (EO) sterilization, shipping, and storage. Materials possessing high glass transition temperatures may not necessarily possess other characteristics that are desirable such as absorbability. Residual stresses are believed to be the main cause of part shrinkage and warpage. Parts may warp or distort dimensionally upon ejection from the mold, during the injection molding cycle, or upon exposure to elevated temperatures, encountered during normal storage or shipping of the product; particularly troublesome is exposure to even slightly elevated temperatures in the presence of plasticizers such as EO encountered during sterilization.

There have been attempts in the prior art to address the problem of lack of dimensional stability in medical devices thermally formed from melt blended absorbable polymers. Smith, U.S. Pat. No. 4,646,741, discloses a melt blend of a lactide/glycolide copolymer and poly(p-dioxanone) used to make surgical clips and two-piece staples. The melt blends of Smith provide molded articles possessing dimensional stability; Smith requires that the amount of poly(p-dioxanone) in the blend is greater than 25 weight percent and teaches away from lower amounts. The polymer blends of Smith have disadvantages associated with their use to manufacture medical devices, including: limited stiffness or Young's modulus, shorter retention of mechanical properties upon implantation, greater sensitivity to moisture limiting the allowable open storage time during manufacture, and, although difficult to quantify, more difficult thermal processing.

As mentioned previously, residual stresses are believed to be the main cause of part shrinkage and warpage. It is known that flow-induced residual stresses may have an effect upon a thermally molded polymeric medical device. Unstressed, long-chain polymer molecules tend to conform to a random-coil state of equilibrium at temperatures higher than the melt temperature (i.e., in a molten state). During thermal processing (e.g., injection molding), the molecules orient in the direction of flow, as the polymer is sheared and elongated. Solidification usually occurs before the polymer molecules are fully relaxed to their state of equilibrium and some molecular orientation is then locked within the molded part. This type of frozen-in, stressed state is often referred to as flow-induced residual stress. Anisotropic, non-uniform shrinkage and mechanical properties in the directions parallel and perpendicular to the direction of flow are introduced because of the stretched molecular structure.

Cooling can also result in residual stresses. For example, variation in the cooling rate from the mold wall to its center can cause thermally-induced residual stress. Furthermore, asymmetrical thermally-induced residual stress can occur if the cooling rate of the two surfaces is unbalanced. Such unbalanced cooling will result in an asymmetric tension-compression pattern across the part, causing a bending moment that tends to cause part warpage. Consequently, parts with non-uniform thickness or poorly cooled areas are prone to unbalanced cooling, and thus to residual thermal stresses. For moderately complex parts, the thermally-induced residual stress distribution is further complicated by non-uniform wall thickness, mold cooling, and mold constraints.

It should be noted that a common, conventional method of sterilization is exposure to ethylene oxide gas in a sterilization process cycle. Absorbable polymeric devices are frequently sterilized by exposure to ethylene oxide (EO) gas. EO can act as a plasticizer of lactide-glycolide copolymers, and can lower the $T_g$ slightly; this may result in 'shrinkage' and/or 'warpage' of an injection-molded part, especially when exposed to temperatures higher than the $T_g$. This adds additional processing and handling challenges when using lactide-glycolide polymeric materials for absorbable medical devices. It should be noted that the EO sterilization process not only exposes the part to EO gas, it also exposes the part to elevated temperatures. This usually requires limiting the treatment to only slightly elevated temperatures increasing processing difficulty. Because EO can act as a plasticizer of synthetic absorbable polyesters, the problems of shrinkage and warpage and general dimensional instability are often exacerbated.

There are a number of processing methods conventionally used to reduce or eliminate shear stresses during processing. Process conditions and design elements that reduce shear stress during cavity filling will help to reduce flow-induced residual stress. Polymeric parts are often heat treated (thermally annealed) to alter their performance characteristics. The reason for the heat treatment processing is to mature the morphological development of the polymer, for example crystallization and/or stress relaxation. If done successfully, the resulting part may exhibit better dimensional stability and may exhibit better mechanical strength; mechanical property retention post-implantation may be affected as well.

Injection molded parts ejected from the injection molding machine that are not already distorted, can be cooled/quenched to room temperature and may appear to be dimensionally sound. Stresses, however, are usually still present and can drive distortion any time the polymer chains are allowed to mobilize. As previously described, this can happen with an increase in temperature or exposure to a plasticizer such as EO gas. In order to overcome this potential driving force for dimensional distortion, a number of strategies have been taken; these include (thermal) annealing.

If the part can be dimensionally constrained, thermal annealing can be employed towards two goals: one is to attempt to reduce the amount of molecular orientation in the polymer chains, also known as stress reduction; and, another is to increase the crystallinity in the part to increase the mechanical rigidity to resist distortion.

With some polymers that readily crystallize, one might be able to crystallize the part while it is still in the mold, but this is an unusual situation. Here the mold cavity not only acts to define the shape of the part, it can act to restrain the shape of the part during the crystallization process. With more-difficult-to-crystallize polymers, the cycle time becomes prohibitively long, and the injection molding process becomes impractical. Thus, the part needs to be ejected from the mold before complete polymer morphology development takes place.

Injection molded parts prepared from semi-crystalline polymers can often be annealed by thermal treatment to increase crystallinity level and complete their polymer morphology development. Often the parts must be physically constrained to avoid the distortion one is attempting to avoid. Once crystallized, the part has increased mechanical rigidity to resist distortion if exposed to normally distorting conditions. Providing suitable physical constraint is often difficult, as it is often labor intensive and economically taxing.

Annealing the ejected part without need for physical constraint is preferred; however what often happens is that the part distorts during the annealing process rendering the part unacceptable for its intended use.

It is known in the industry to anneal parts to reduce molded-in-stresses by thermal relaxation. The time and temperature required to relieve stress varies but must often be done below the $T_g$ to avoid gross distortion. Even then the results can vary greatly. It is more difficult to reduce stress levels, without causing distortion, in higher molecular weight resins. It would be relatively easy to reduce molded-in-stresses by thermal relaxation in low molecular weight, high flow polyesters, as compared to higher molecular weight polyesters.

Regarding the molecular weight of the polymer blend, higher molecular weight usually develops higher stress levels and requires longer times/higher temperatures for stress relaxation. Although this is the case, higher molecular weight is often needed to achieve high mechanical properties and biological performance. This situation often presents a problem for the device manufacturer.

In order to impart more crystallinity to increase mechanical rigidity to better resist distortion, or to reduce molecular orientation in order to lower the driving force for distortion, the parts would ideally be processed by thermal treatment (annealing) at a temperature which does not cause distortion. Unfortunately, due to the nature of the synthetic absorbable polyesters commonly employed, this treatment often needs to be above their glass transition temperature where distortion is nearly impossible to avoid.

Consider for example, polylactide homopolymeric or poly(lactide-co-glycolide) copolymeric devices. The stressed polymer chains of these injection-molded parts will tend to relax and return to their natural state ("random three-dimensional coils") when heated to or above their glass transition temperatures. This will be observed as warpage, shrinkage or general dimensional deformation. It is a general practice in the industry when producing molded polylactide-based parts, not to anneal them because of this potential deformation. These as-molded polylactide parts are of very low crystallinity, if not outright amorphous or non-crystalline, and will then tend to deform if exposed to temperatures at or above their respective glass transition temperatures if they possess moderate residual stress. It would be advantageous to be able to anneal such parts to induce crystallinity so that they may develop the high rigidity to remain dimensionally stable under conditions normally encountered during EO sterilization, shipping, and storage.

There are medical applications that require the medical device to display sufficient column strength such as in the case of an implantable staple or a tack. Clearly, for a device having such a requirement with a smaller cross-sectional area, the polymer from which it was formed must be inherently stiff if the tack is to function properly for the intended application.

To achieve higher stiffness in a melt blend of a lactide/glycolide copolymer and poly(p-dioxanone), one needs to minimize the amount of poly(p-dioxanone). Contrary to what Smith teaches, it has been found that dimensional stability can be achieved in parts molded from a blend of a lactide-rich copolymer and poly(p-dioxanone), in which the levels of poly(p-dioxanone) are lower than 25 weight percent. The addition of the poly(p-dioxanone), even at these low levels, enhances the ability to achieve dimensional stability in the final part. It remains, however, that the addition of any amount of poly(p-dioxanone) is expected to lower the stiffness of the blend at constant crystallinity level.

Even though such polymer blends are known, there is a continuing need in this art for novel absorbable polymeric materials that provide a medical device with improved characteristics including stiffness, retained strength in vivo (in situ), dimensional stability, absorbability in vivo, and manufacturability, along with a need for novel medical devices made from such polymeric materials, and novel methods of manufacturing medical devices from such polymeric materials.

SUMMARY OF THE INVENTION

It is an object of the present invention to provide novel absorbable polymer blends that can be used in manufacturing processes to produce novel absorbable medical devices and medical device components by melt processes, such as injection molding, and by other processes, wherein the devices or components have superior mechanical properties (such as high stiffness and column strength), superior mechanical property retention post-implantation (such as superior breaking strength retention), acceptable absorption rates, and superior dimensional stability.

Accordingly, a novel absorbable polymer blend composition is disclosed. The polymer blend has a first absorbable polymer and a second absorbable polymer. The first polymer comprises at least 50 weight percent of a lactide-rich polymer comprising about 100 mole percent to about 70 mole percent polymerized lactide and about 0 mole percent to about 30 mole percent polymerized glycolide, and the second polymer comprises poly(p-dioxanone). The maximum weight percent of poly(p-dioxanone) in the blend is 50 weight percent and the minimum weight percent of poly(p-dioxanone) in the blend is sufficient so that the polymer blend provides dimensional stability to a manufactured article. The first absorbable polymer, or the second absorbable polymer, or the first absorbable polymer and the second absorbable polymer are bimodal molecular weight distribution polymers. That is, they have a bimodal molecular weight distribution. Each bimodal molecular weight distribution polymers comprises a blend of from about 60 to 95 wt. % of a first component polymer having a first weight average molecular weight distribution between about 50,000 to about 500,000 Daltons; and, from about 5 to 40 wt. % of a second component polymer having a second weight average molecular weight distribution between about 10,000 to about 50,000 Daltons. Additionally, the weight average molecular weight ratio of said first molecular weight distribution to said second molecular weight distribution is at least about two to one.

Another aspect of the present invention is an absorbable polymer blend. The blend has a first absorbable polymer comprising at least 50 weight percent of a lactide-rich polymer comprising about 100 mole percent to about 70 mole percent polymerized lactide and about 0 mole percent to about 30 mole percent polymerized glycolide, and, a second absorbable polymer comprising poly(p-dioxanone). The maximum weight percent of poly(p-dioxanone) in the blend is 50 weight percent and the minimum weight percent of poly(p-dioxanone) in the blend is sufficient so that the polymer blend effectively provides dimensional stability to a manufactured article. One or both of the first absorbable polymer and the second absorbable polymer are bimodal molecular weight distribution polymers. Each bimodal molecular weight distribution polymer comprises a blend of:

(a) from about 60 to 95 wt. % of a first component polymer having a first weight average molecular weight between about 50,000 to about 500,000 Daltons; and (b) from about 5 to 40 wt. % of a second component polymer having a second weight average molecular weight between about 10,000 to about 50,000 Daltons, the weight average molecular weight ratio of said first molecular weight to said second molecular weight is at least about two to one.

The minimum weight percent of poly(p-dioxanone) in the blend depends upon the molar amount of polymerized lactide in the lactide-rich polymer and is calculated by the expression:

Weight Percent Poly(p-dioxanone)=(215.6212/Mole Percent Polymerized Lactide)$^{2.7027}$−1.177 when the lactide-rich polymer has a unimodal molecular weight distribution and the poly(p-dioxanone) has a bimodal molecular weight distribution. The polymer blend provides dimensional stability to a manufactured article.

Yet another aspect of the present invention is an absorbable polymer blend. The blend has a first absorbable polymer comprising at least 50 weight percent of a lactide-rich polymer comprising about 100 mole percent to about 70 mole percent polymerized lactide and about 0 mole percent to about 30 mole percent polymerized glycolide, and, a second absorbable polymer comprising poly(p-dioxanone). The maximum weight percent of poly(p-dioxanone) in the blend is 50 weight percent and the minimum weight percent of poly(p-dioxanone) in the blend is sufficient so that the polymer blend effectively provides dimensional stability to a manufactured article. One or both of the first absorbable polymer and the second absorbable polymer are bimodal molecular weight distribution polymers. Each bimodal molecular weight distribution polymer comprises a blend of:

(a) from about 60 to 95 wt. % of a first component polymer having a first weight average molecular weight between about 50,000 to about 500,000 Daltons; and, (b) from about 5 to 40 wt. % of a second component polymer having a second weight average molecular weight between about 10,000 to about 50,000 Daltons, the weight average molecular weight ratio of said first molecular weight to said second molecular weight is at least about two to one.

The minimum weight percent of poly(p-dioxanone) in the blend depends upon the molar amount of polymerized lactide in the lactide-rich polymer and is calculated by the expression:

Weight Percent Poly(p-dioxanone)=(215.6212/Mole Percent Polymerized Lactide)$^{2.7027}$−4.877 when the lactide-rich polymer has a bimodal molecular weight distribution and the poly(p-dioxanone) has a unimodal or bimodal molecular weight distribution. The polymer blend provides dimensional stability to a manufactured article.

Still yet another aspect of the present invention is a medical device made from the above-described novel polymer blends.

A further aspect of the present invention is a method of manufacturing a medical device from the above-described polymer blends.

These and other aspects and advantages of the present invention will become more apparent from the following description and accompanying drawings.

DETAILED DESCRIPTION OF THE INVENTION

Problem to be Solved I

Figure 1:
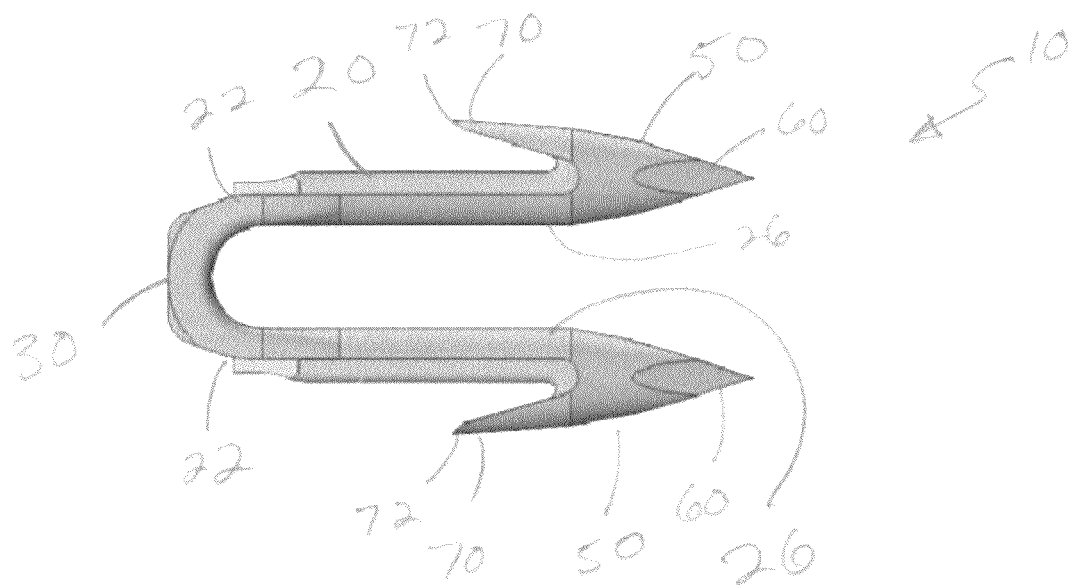
FIG. 1 is a drawing of an implantable staple or tack/strap demonstrating the present invention, and shows a device with a small cross-sectional area.

Most absorbable resins have rather low glass transition temperatures leading to low deflection temperatures unless the formed part is crystallized to a sufficient extent. The rate of crystallinity development during the injection molding process to form a given part is very important from an economic standpoint (e.g., parts made/hour), as cycle times increase to allow sufficient crystallization in the mold. But perhaps more importantly from a performance standpoint, long cycle times will result in long residence times in the barrel leading to degradation of the resin. This degradation lowers the molecular weight of the resin resulting in lower mechanical properties and possible faster loss of mechanical properties with time post-implantation.

It is thus desired to increase the rate of crystallization of the absorbable resin to aid the development of dimensional stability in molded parts.

It is further desired to increase the rate of crystallization of the absorbable resin to lower the cycle time during injection molding to form parts at a faster rate, thus providing economic advantage.

It is still further desired to increase the rate of crystallization of the absorbable resin to lower the cycle time during injection molding to form molded parts to decrease the residence time of the resin in the barrel to avoid unwanted thermal degradation. This is expected to result in higher molecular weight parts with higher performance characteristics; the minimization of the degradation during molding also results in more robust manufacturing processes.

A related problem is the ultimate level of crystallinity developed (as opposed to the aforementioned crystallization rate). A sufficient level of crystallinity must be developed to minimize part distortion and other forms of dimensional instability such as shrinkage or warpage. The higher the molecular orientation exhibited in an injection molded part, the greater will be the driving force for distortion. With greater molecular orientation, a higher level of crystallinity is needed to resist distortion in its various forms. Additionally, synthetic absorbable polymers that have lower glass transition temperature are more susceptible to distortion, again requiring the development of a higher level of crystallinity in the part.

It is thus further desired to increase the percent of crystallization developed in molded parts to increase the dimensional stability of said parts.

Solution to Problem I

Aid the Development of Dimensional Stability/Form Parts at a Faster Rate/Increase Performance Characteristics/Provide More Robust Manufacturing Processes/Increase Stiffness It was found that we can provide an absorbable polymer blend of at least two absorbable polymers that finds utility in the manufacture of implantable medical devices that possess good dimensional stability. This has been achieved by providing the first absorbable polymer selected from either a poly(lactide-co-glycolide) copolymer or a polylactide homopolymer in a form having a bimodal molecular weight distribution, and blending it with poly(p-dioxanone). It can be also achieved by blending a first absorbable polymer selected from either a poly(lactide-co-glycolide) copolymer or a polylactide homopolymer with a second absorbable polymer, poly (p-dioxanone) in a form having a bimodal molecular weight distribution. Alternately, this can be achieved by providing the first absorbable polymer selected from either a poly(lactide-co-glycolide) copolymer or a polylactide homopolymer in a form having a bimodal molecular weight distribution, and blending it with poly(p-dioxanone) in a form having a bimodal molecular weight distribution.

Providing a faster crystallization rate aids the development of dimensional stability in a molded part; one might be able to form parts at a faster rate, and with lower cycle time, lower the amount of thermal degradation that usually occurs during long cycle times, thus increasing performance characteristics. With faster crystallization and lower degradation during thermal processing, more robust manufacturing processes are achieved. Finally, with higher crystallinity levels achieved in the molded parts, part stiffness may be increased.

It is to be noted that with the faster crystallization rate, and the development of higher percent crystallinity being achieved in molded parts, one might be additionally able to shift the composition of the blend to lower poly(p-dioxanone) levels. With the reduction of the low $T_g$ polymer component, poly(p-dioxanone), stiffness is further increased.

An advantage of the present inventive blends is the ability to crystallize fast; this is particularly important for processing, especially for injection molding. The faster that an article crystallizes in a mold, the shorter the cycle time that is needed for developing a morphology that allows increased dimensional stability and avoids warping. There is additionally an economic benefit in reducing cycle time. However, shortened cycle times also reduce the time the polymer resides in the machine at elevated temperatures. This reduces the amount of degradation in the form of molecular weight reduction and discoloration that may occur, further improving part quality. Retention of a molecular weight may additionally lead to higher mechanical properties and the retention of molecular properties post-implantation. The amount of crystallinity needed in the part prior to ejection from the mold depends on the glass transition temperature of the resin as well as the molecular weight of the resin. The lower the glass transition temperature of the resin, the higher the level of crystallinity that is needed to provide dimensional stability in a molded part.

In some cases, it is advantageous to have the molded part crystallize outside the mold, that is, after the part has been ejected from the molding machine. The ability for the part to crystallize at a rapid rate is advantageous from a processing standpoint. Rapid crystallization is very helpful in providing dimensional stability of the part as it is undergoing further processing. It will be shown that the polymer blends of the present invention crystallize at a faster rate than the control (the blend based on components having unimodal molecular weight distribution).

Problem to be Solved II

At a given composition, that is, wherein the blend component ratios remain invariant, there are instances when higher stiffness is required; this can be interpreted as requiring a higher modulus. At a given composition one might increase the percent crystallization developed in the molded part to increase the stiffness of said part. The problem then is: "How to increase the percent crystallization level in a molded part other than providing thermal treatments?"

Solution to Problem II

Increase Stiffness at a Given Overall Composition

The present invention additionally provides a polymer blend suitable for making implantable medical devices that still possesses good dimensional stability in molded parts that have higher moduli than previously available absorbable blends of the same overall composition by virtue of selecting preferred blend components exhibiting bimodal molecular weight distributions.

Note that in Problem/Solution I, the poly(p-dioxanone) weight percent may be lowered by increasing the crystallization rate, and the overall crystallinity developed, in the poly(lactide-co-glycolide) copolymer. Here we are considering the case wherein the blend component ratios remain invariant.

It has been have found that by providing the first absorbable polymer, the second absorbable polymer, or both absorbable polymers having bimodal molecular weight distributions. The present invention provides a polymer blend suitable for making implantable medical devices that still possesses good dimensional stability in molded parts that have higher moduli than previously available absorbable blends by virtue of increasing the crystallization rate, and the overall crystallinity developed in the molded part.

Besides the rate or kinetics of crystallization, the ultimate level of crystallinity developed in the part is also of great importance. If the level of crystallinity developed in the part is insufficient, the part may not possess the dimensional stability required. Because the inventive blends crystallize faster than controls, under certain conditions the inventive blends possess higher crystallinity levels which can lead to articles having better mechanical properties, such as being stiffer. It will be shown that even when fully annealed, the crystallinity levels of the inventive blends are higher than controls.

Problem to be Solved III

Increase the Rate of Absorption at a Given Overall Composition

For a given modulus level, there may be a need to increase the rate of absorption to decrease the time the device is present in the body.

Solution to Problem III

In an effort to increase the absorption rate of an implanted medical device having dimensional stability, we provide an absorbable polymer blend of at least two absorbable polymers that finds utility in the manufacture of implantable medical devices that possess good dimensional stability. This has achieved by providing the first absorbable polymer selected from the group of a poly(lactide-co-glycolide) copolymer or a polylactide homopolymer in a form having a bimodal molecular weight distribution, and blending it with poly(p-dioxanone). It can be also achieved by blending a first absorbable polymer selected from a poly(lactide-co-glycolide) copolymer or a polylactide homopolymer with a second absorbable polymer, poly(p-dioxanone) in a form having a bimodal molecular weight distribution. Alternately, this can be achieved by providing the first absorbable polymer selected from a poly(lactide-co-glycolide) copolymer or a polylactide homopolymer in a form having a bimodal molecular weight distribution, and blending it with poly(p-dioxanone) in a form having a bimodal molecular weight distribution.

Providing blend components possessing bimodal molecular weight distributions enables the preferred inventive blends to degrade faster post-implantation than the corresponding blends made with blend components based on unimodal molecular weight polymers, while adequately stabilizing the molded part so as to undergo processing to avoid warping and dimensional instability during further in-house processing, sterilization, packaging, transportation, storage, etc. It is pointed out that degradation post-implantation is meant to include faster loss of mechanical properties with time in the body, as well as decreasing the time necessary to absorb in the body.

U.S. Pat. Nos. 8,450,431 B2 and 8,236,904 B2 are incorporated by reference in their entirety. In addition, commonly-assigned, co-pending U.S. Patent Publication No. 2012-0071566 published Mar. 22, 2012 is incorporated by reference in its entirety. Although the terms "bimodal" or "bimodal molecular weight distribution" will be used in this application, what is meant are molecular weight distributions having broader $M_w/M_n$ values that are expected from "normally distributed" polyesters. By $M_w$ we mean weight average molecular weight, and by $M_n$ we mean number average molecular weight, concepts well known in the field of polymer science. "Normally distributed" polyesters typically have $M_w/M_n$ values approaching 2 at molecular weights necessary to exhibit high mechanical properties ($M_w/M_n = [1+p]$ where "p" is the extent of reaction and approaches a value of close to one at even moderately high molecular weight). Gel permeation chromatography [GPC] might be utilized to detect a bimodal distribution. However in cases where the amount of the minor component is small, it may be difficult to ascertain. In these cases, an examination of the $M_w/M_n$ values of the polyester under question might be called for. See Table 1 below for some molecular weight data on the (co)polymers having a bimodal molecular weight distribution. These bimodal (co)polymers are then further blended to result in the blends of the present invention.

TABLE 1

|   |   | Expected | | Bimodal (Co)Polymer | | |
|---|---|---|---|---|---|---|
|   |   | Mw | Mn | Mw | Mn | Mw/Mn |
| 1 | 95.0% High | 500,000 | 250,000 | 477,500 | 172,414 | 2.77 |
|   | 5.0% Low | 50,000 | 25,000 |   |   |   |
| 2 | 60.0% High | 500,000 | 250,000 | 320,000 | 54,348 | 5.89 |
|   | 40.0% Low | 50,000 | 25,000 |   |   |   |
| 3 | 60.0% High | 500,000 | 250,000 | 304,000 | 12,136 | 25.05 |
|   | 40.0% Low | 10,000 | 5,000 |   |   |   |
| 4 | 95.0% High | 50,000 | 25,000 | 48,750 | 23,810 | 2.05 |
|   | 5.0% Low | 25,000 | 12,500 |   |   |   |
| 5 | 60.0% High | 50,000 | 25,000 | 40,000 | 17,857 | 2.24 |
|   | 40.0% Low | 25,000 | 12,500 |   |   |   |
| 6 | 95.0% High | 80,000 | 40,000 | 78,000 | 38,095 | 2.05 |
|   | 5.0% Low | 40,000 | 20,000 |   |   |   |
| 7 | 60.0% High | 80,000 | 40,000 | 64,000 | 28,571 | 2.24 |
|   | 40.0% Low | 40,000 | 20,000 |   |   |   |
| 8 | 95.0% High | 80,000 | 40,000 | 77,000 | 34,783 | 2.21 |
|   | 5.0% Low | 20,000 | 10,000 |   |   |   |
| 9 | 60.0% High | 80,000 | 40,000 | 56,000 | 18,182 | 3.08 |
|   | 40.0% Low | 20,000 | 10,000 |   |   |   |
| 10 | 80.0% High | 80,000 | 40,000 | 68,000 | 25,000 | 2.72 |
|   | 20.0% Low | 20,000 | 10,000 |   |   |   |

The novel polymer blends of the present invention are made from absorbable polyester polymers and copolymers having bimodal molecular weight distributions. Preferably, one of the blend components is either poly(L(−)-lactide), poly(D(+)-lactide), or a lactide-rich lactide/glycolide copolymer possessing a bimodal molecular weight distribution. The lactide-rich polymer comprise about 100 mole percent to about 70 mole percent polymerized lactide and about 0 mole percent to about 30 mole percent polymerized glycolide. The other blend component is the absorbable polymer poly(p-dioxanone). The poly(p-dioxanone) may have either a unimodal or a bimodal molecular weight distribution. In the case when the poly(p-dioxanone) has a bimodal molecular weight distribution, the lactide-based polymer may have a unimodal bimodal molecular weight distribution.

It is to be understood that in the case of the lactide-rich lactide/glycolide copolymer, the lactide is ether substantially L(−)-lactide or D(+)-lactide; specifically avoiding meso-lactide or racemic-lactide, the latter a 50/50 blend of L(−)-lactide and D(+)-lactide. It is further understood that the stereocomplex made of poly(L(−)-lactide) and poly(D(+)-lactide) may be utilized, of any proportion, with the 50/50 mixture being particularly advantageous when high strength or high modulus is required. Further, the lactide-rich lactide/glycolide copolymer may be a stereocomplex of a poly(L(−)-lactide-co-glycolide) and poly(D(+)-lactide-co-glycolide), of any proportion, with the 50/50 mixture again being particularly advantageous.

It is to be understood that the lactide-based polymer component may be bimodal in nature or the p-dioxanone-based polymer component may be bimodal in nature, or both the lactide-based and the p-dioxanone-based components may be bimodal in nature. Consider, now, the first component, specifically one having a bimodal molecular weight distribution. This first component can be a bimodal molecular weight blend made of the poly(L(−)-lactide), poly(D(+)-lactide), poly(L(−)-lactide)/poly(D(+)-lactide) stereocomplex, or a lactide-rich lactide/glycolide copolymer can be made from a bimodal polymer composition comprising: a first amount of a polylactide or lactide-rich lactide/glycolide copolymer having first a weight average molecular weight between about 50,000 to about 500,000 Daltons; and a second amount of a polylactide or lactide-rich lactide/glycolide copolymer having a second weight average molecular weight between about 10,000 to about 50,000 Daltons. The weight average molecular weight ratio of the first molecular weight distribution to the second molecular weight distribution is at least about two to one; wherein a substantially homogeneous blend of the first and second amounts of the absorbable polymer is formed in a ratio of between about 60/40 to 95/5 Weight/Weight percent.

It is to be understood that in the case of a unimodal molecular weight distribution first component, it can be comprised of poly(L(−)-lactide), poly(D(+)-lactide), poly(L(−)-lactide)/poly(D(+)-lactide) stereocomplex, or a lactide-rich lactide/glycolide copolymer having a first weight average molecular weight between about 50,000 to about 500,000 Daltons.

The first bimodal molecular weight blend component [the poly(L(−)-lactide), poly(D(+)-lactide), poly(L(−)-lactide)/poly(D(+)-lactide) stereocomplex, lactide-rich lactide/glycolide copolymer, or stereocomplex of poly(L(−)-lactide-co-glycolide) and poly(D(+)-lactide-co-glycolide)] will be manufactured in a conventional manner. A preferred manufacturing method is as follows. The first step in the process is to conduct a ring-opening polymerization (ROP) of an appropriate lactide monomer [L(−) or D(+), etc.] and glycolide monomer in the molar ratio of lactide to glycolide of 100/0 to 70/30 with the monomer to initiator ratio of about 400:1 to about 2,000:1. The next step is to conduct an ROP of an appropriate lactide monomer [L(−) or D(+), etc.] and glycolide monomers in the molar ratio of lactide to glycolide of 100/0 to 70/30 with the monomer to initiator ratio of about 100:1 to about 400:1. The final step is to blend the first component and the second component by either using a solvent or melt blending techniques, with melt blending techniques preferred.

The second blend component, poly(p-dioxanone), can be of unimodal or bimodal molecular weight distribution in nature. In the latter case, the second blend component having a bimodal molecular weight distribution may comprise: a first amount of a poly(p-dioxanone) polymer having a first weight average molecular weight between about 50,000 to about 500,000 Daltons; and a second amount of a poly(p-dioxanone) polymer having a second weight average molecular weight between about 10,000 to about 50,000 Daltons. The weight average molecular weight ratio of the first molecular weight distribution to the second molecular weight distribution is at least about two to one. A substantially homogeneous blend of the first and second amounts of the absorbable polymer is formed in a ratio of between about 60/40 to 95/5 Weight/Weight percent.

The second component, unimodal poly(p-dioxanone) or a bimodal molecular weight blend of poly(p-dioxanone) useful in the novel polymer blends of the present invention, is manufactured in a conventional manner. For example, the first step is to conduct an ROP of p-dioxanone with a monomer to initiator ratio of about 400:1 to about 2,000:1 to result in a higher molecular weight poly(p-dioxanone). The next or second step is to conduct an ROP of p-dioxanone with a monomer to initiator ratio of about 100:1 to about 400:1 to result in a lower molecular weight poly(p-dioxanone), provided that the resulting weight average molecular weight ratio of this second p-dioxanone polymer is no more than half of the weight average molecular weight ratio of the first p-dioxanone polymer. The third or final step is to blend the first and second p-dioxanone polymer components by either using a solvent or melt blending techniques, with melt blending techniques preferred.

It is to be understood that one might advantageously reduce the number of (solution or melt) blending operations required by combining multiple blend components in a single blending procedure. For example, one might combine a higher molecular weight lactide-rich lactide/glycolide copolymer, a lower molecular weight lactide-rich lactide/glycolide copolymer, a higher molecular weight poly(p-dioxanone), and a lower molecular weight poly(p-dioxanone) in a single melt blending operation.

The novel polymer blends of the present invention can be manufactured from the individual components in a variety of conventional manners using conventional processing equipment. Examples of manufacturing processes include chemical reactions of the ring-opening and polycondensation type, devolitilization and resin drying, dry blending in a tumble dryer, solution blending, extrusion melt-blending, injection molding, thermal annealing, and ethylene oxide sterilization processes. An alternate to dry blending with subsequent melt blending of the mixture can include the use of two or more feeders, preferably loss-in-weight feeders, that supply the components to be blended to an extruder; the extruder can be of the single screw or twin screw variety. Alternately, multiple extruders can be used to feed melts of the blend components, such as in co-extrusion. It should be noted that devolatilization of the resin components or of the blend to remove residual monomer and for purposes of resin drying may be accomplished by a variety of means including vacuum tumble drying using an appropriate temperature scheme or fluidized bed drying, again using an appropriate temperature scheme.

For the purpose of the present invention, blends of this type can be produced in a similar manner with different compositions. Alternately one may make the inventive blends by combining the polylactide or poly(lactide-co-glycolide)copolymer of normal molecular weight distribution with the poly(p-dioxanone) of standard molecular weight and standard normal molecular weight distribution and the poly(p-dioxanone) of lower molecular weight and standard normal molecular weight distribution; that is, all of the ingredients are dry mixed together and then undergo a single melt blending.

Further, one may make embodiments of the present invention by combining a lactide/glycolide [L/G] copolymer possessing a bimodal molecular weight distribution with a poly (p-dioxanone) of standard molecular weight distribution or with a bimodal molecular weight distribution. These variants or embodiments can be made by first making the bimodal component in a separate melt blending operation, and then combining components in a second melt blending operation, or by combining all of the components in a single operation. This may be a preferred method of making bimodal blends of the present invention.

The blends of the present invention may be made by thermal processes. Examples of conventional thermal processes that may be utilized to produce the polymer blends of the present invention include melt blending in an extruder, which can include twin screw blending or single screw extrusion, co-extrusion, twin screw blending with simultaneous vented-screw vacuum devolitilization, vacuum tumble drying with thermal devolitilization, monomer removal by solvent extraction at elevated temperature, and resin annealing.

The polymer components, as well as the blends of the present invention can be sized by conventional processes such as pelletization, granulation, and grinding.

A further embodiment of the present invention is feeding appropriately-sized particles of the blend components directly to the hopper of the injection molding machine. The size of the particles can be easily determined experimentally. If the particles are in the shape of cylinders, a diameter between 0.060 and 0.090 inches might be appropriate providing an average pellet weight between about 5 and 20 mg. Suitable ground material might be produced employing a 3/16" screen at the discharge port of a Cumberland grinder. It would be apparent to one skilled in the art that this technique may be applied to other processing methodologies, such as, but not limited to, film or fiber extrusion. Limiting the thermal history of the polymer blend components is advantageous in that it avoids the possibility of premature degradation. Additional methods of thermal processing can include processes such as injection molding, compression molding, blow molding, blown film, thermoforming, film extrusion, fiber extrusion, sheet extrusion, profile extrusion, melt blown nonwoven extrusion, co-extrusion, tube extrusion, foaming, rotomolding, calendaring, and extrusion. As noted earlier, appropriately-sized particles of the blend components can be blended in the melt using these thermal processing means.

Other examples of manufacturing process equipment include chemical reactors ranging in size from two-gallon to seventy-five gallon capacity, process devolatilization dryers ranging from one cubic feet to twenty cubic feet, single and twin-screw extruders from about one inch to about three inches in diameter, and injection molders ranging from about seven to about 40 tons in size.

If desired, the polymer blends of the present invention may contain additional conventional components and therapeutic agents. The components, additives or agents will be present to provide additional effects to the polymer blends and medical devices of the present invention including antimicrobial characteristics, controlled drug elution, radio-opacification, and osseointegration.

Such other components will be present in a sufficient amount to effectively provide for the desired effects or characteristics. Typically, the amount of the components will be about 0.1 weight percent to about 20 weight percent, more typically about 1 weight percent to about 10 weight percent and preferably about 2 weight percent to about 5 weight percent.

Examples of antimicrobial agents include the polychloro phenoxy phenols such as 5-chloro-2-(2,4-dichlorophenoxyl) phenol (also known as Triclosan).

Examples of radio-opacification agents include barium sulfate while examples of osseointegration agents include tricalcium phosphate.

The variety of therapeutic agents that can be used in the polymer blends of the present invention is vast. In general, therapeutic agents which may be administered via pharmaceutical compositions of the invention include, without limitation, antiinfectives, such as antibiotics and antiviral agents; analgesics and analgesic combinations; anorexics; antihelmintics; antiarthritics; antiasthmatic agents; adhesion preventatives; anticonvulsants; antidepressants; antidiuretic agents; antidiarrheals; antihistamines; anti-inflammatory agents; antimigraine preparations; contraceptives; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators, including general coronary, peripheral and cerebral; central nervous system stimulants; cough and cold preparations, including decongestants; hormones, such as estradiol and other steroids, including corticosteroids; hypnotics; immunosuppressives; muscle relaxants; parasympatholytics; psychostimulants; sedatives; tranquilizers; naturally derived or genetically engineered proteins, polysaccharides, glycoproteins, or lipoproteins; oligonucleotides, antibodies, antigens, cholinergics, chemotherapeutics, hemostatics, clot dissolving agents, radioactive agents and cystostatics. Therapeutically effective dosages may be determined by in vitro or in vivo methods. For each particular additive, individual determinations may be made to determine the optimal dosage required. The determination of effective dosage levels to achieve the desired result will be within the realm of one skilled in the art. The release rate of the additives may also be varied within the realm of one skilled in the art to determine an advantageous profile, depending on the therapeutic conditions to be treated.

Suitable glasses or ceramics include, but are not limited to phosphates such as hydroxyapatite, substituted apatites, tetracalcium phosphate, alpha- and beta-tricalcium phosphate, octacalcium phosphate, brushite, monetite, metaphosphates, pyrophosphates, phosphate glasses, carbonates, sulfates and oxides of calcium and magnesium, and combinations thereof.

Suitable polymers that may be included in the polymer blends of the present invention include: suitable biocompatible, biodegradable polymers which may be synthetic or natural polymers. Suitable synthetic biocompatible, biodegradable polymers include polymers selected from the group consisting of aliphatic polyesters, poly(amino acids), copoly (ether-esters), polyalkylenes oxalates, polyamides, tyrosine derived polycarbonates, poly(iminocarbonates), polyorthoesters, polyoxaesters, polyamidoesters, polyoxaesters containing amine groups, poly (anhydrides), polyphosphazenes, polydiglycolates, and combinations thereof. It is to be understood that inclusion of additional suitable polymers is dependent upon obtaining dimensional stability in the fabricated device.

For the purposes of this invention the above optional aliphatic polyesters include, but are not limited to, homopolymers and copolymers of lactide (which include lactic acid, D-, L- and meso lactide), glycolide (including glycolic acid), epsilon-caprolactone, p-dioxanone (1,4-dioxan-2-one), trimethylene carbonate (1,3-dioxan-2-one), alkyl derivatives of trimethylene carbonate, and blends thereof.

Suitable natural polymers include, but are not limited to collagen, elastin, hyaluronic acid, laminin, gelatin, keratin, chondroitin sulfate and decellularized tissue.

Although not preferred, the medical devices of the present invention may contain nonabsorbable polymers in addition to the absorbable polymer blends of the present invention. Examples of such devices may include but are not limited to meshes, sutures, and staples, where the properties of both the absorbable and nonabsorbable polymers are advantageous.

Suitable nonabsorbable polymers include, but are not limited to acrylics; polyamide-imide (PAI); polyaryletherketones (PEEK); polycarbonates; thermoplastic polyolefins such as polyethylene (PE), polypropylene (PP), polymethylpentene (PMP), and polybutene-1 (PB-1); polyolefin elastomers (POE) such as polyisobutylene (PIB), ethylene propylene rubber (EPR); polybutylene terephthalate (PBT); polyethylene terephthalates (PET); polyamides (PA) such as nylon 6 and nylon 66; polyvinylidene fluoride (PVDF); polyvinylidene fluoride-co-hexafluropropylene (PVDF/HFP); polymethylmethacrylate (PMMA) and combinations thereof and equivalents.

An example of a medical device that can be molded from the polymer blends of the present invention is a tissue tack 10 as seen in FIG. 1. FIG. 1 is a drawing of an implantable staple or tack demonstrating the present invention, and shows a device with a small cross-sectional area. The material of this device must be inherently stiff if the tack is to function properly for the intended application.

Figure 2:
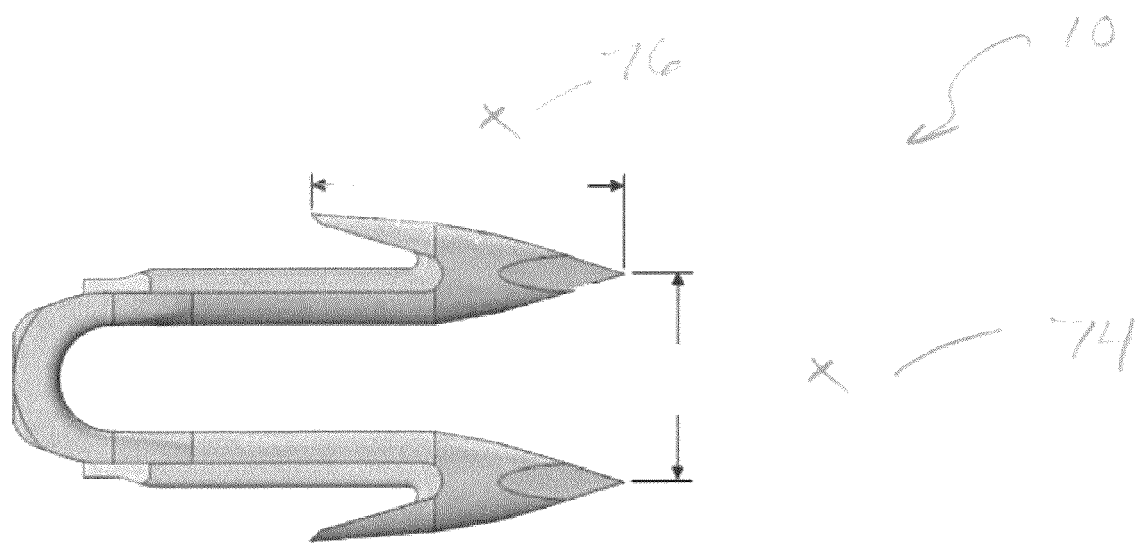
FIG. 2 is a drawing of the device of FIG. 1 showing critical dimensions of said device.

The tack 10 is seen to have two leg members 20 connected by a connecting strap member 30 at their proximal ends 22. The distal ends 26 are seen to have barb members 50 extending distally therefrom. Barb members 50 have distal tissue piercing points 60 and proximal barbs 70 having points 72. Referring to FIG. 2, barb members 50 are seen to have a length 74 shown as dimension Y. The points 60 are seen to be spaced apart by a distance 76 shown as dimension X.

Suitable tacks that can be made from the polymer blends of the present invention are also disclosed and described in commonly-assigned U.S. patent application Ser. Nos. 12/464,143; 12/464,151; 12/464,165; and, 12/464,177, which are incorporated by reference in their entirety.

The dimensional stability of articles molded from the novel polymer blends of the present invention was evaluated. The article chosen for evaluation was a 5 mm laparoscopic device for hernia repair; it was in the form of a staple or strap with legs and tissue holding means to the end of the legs. The device is illustrated in FIG. 2. The article was geometrically complex and was sterilized using conventional ethylene oxide sterilization processes after undergoing an annealing process. The device was used to fixate prosthetic mesh to soft tissue in both laparoscopic and open procedures.

For the device depicted in FIG. 1, the tip-to-tip distance is a critical dimension; see FIG. 2. FIG. 2 is a drawing of the device of FIG. 1 showing the critical dimensions of said device. These dimensions, if changed by lack of dimensional stability, can lead to poor performance and or failure of the device. A tip-to-tip distance of less than 0.115 inches for the articles depicted in FIG. 1 were said to be acceptable, while a tip-to-top distance greater than or equal to 0.115 inches were said to be unacceptable and denoted as "failure mode one" or "fm1". Likewise, the length of the barb members from articles depicted in FIG. 1 were also considered critical dimensions. A barb length of less than or equal to 0.136 inches were considered unacceptable and denoted as "failure mode 2" or "fm2".

Photographic images and dimensions may be captured using a Keyence digital microscope, model VHX-600, with a magnification of 20×.

Figure 3:
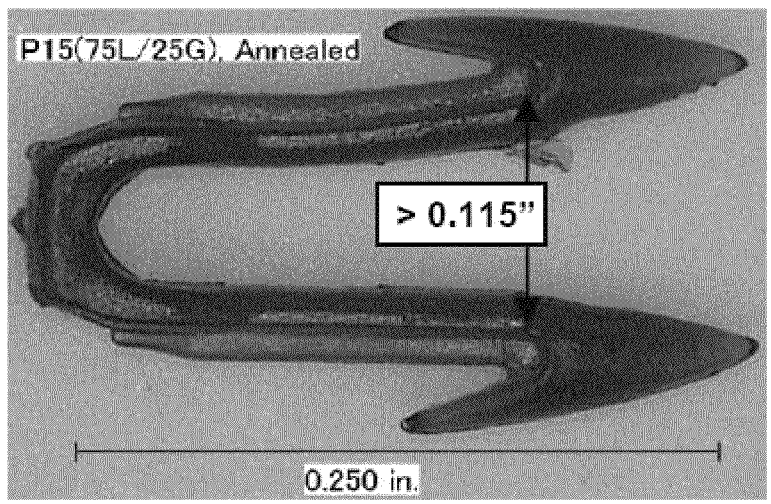
FIG. 3 is a photograph of an injection molded tack/strap of the device of FIG. 1 exhibiting poor dimensional stability and an unacceptable level of warping after thermal annealing.

FIG. 3 is a photograph of an injection molded tack based on the design shown in FIG. 1, made from a polymer composition outside the present invention that displays unacceptable warping after thermal annealing.

Figure 4:
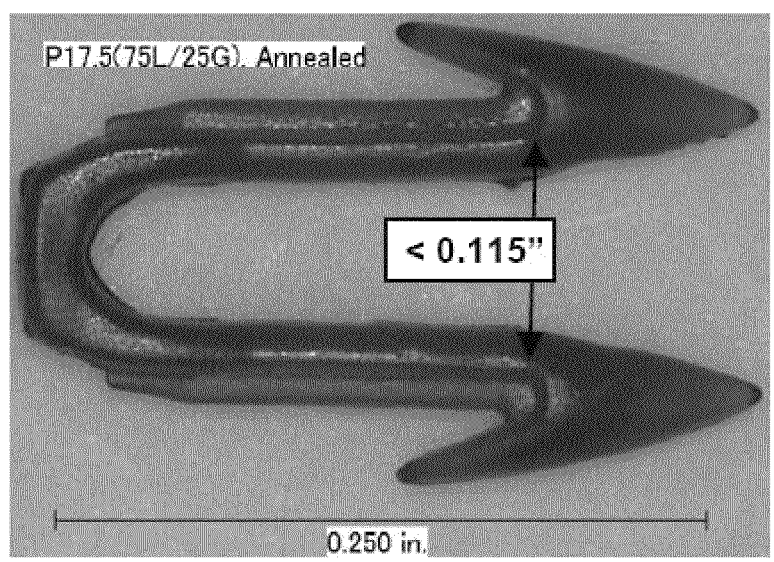
FIG. 4 is a photograph of an injection molded tack/strap of the device of FIG. 1 exhibiting superior dimensional stability and an acceptable level of warping after thermal annealing.

FIG. 4 is a photograph of an injection molded tack based on the design shown in FIG. 1, made from a polymer composition of the present invention that displays acceptable warping after thermal annealing.

It is to be understood that the blends of the present invention can be used to fabricate medical devices using various melt processing techniques. As shown in some of the above examples, injection molding is one of the techniques that are applicable. It is further understood that a variety of designs may be employed utilizing these inventive blends.

Figure 5:
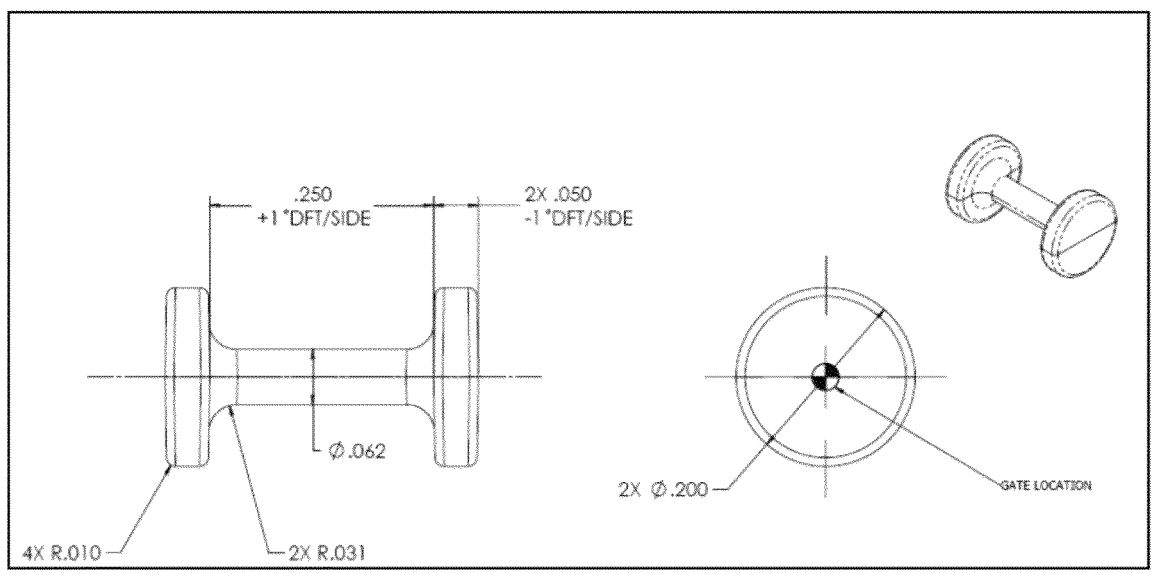
FIG. 5 is a drawing of a dumbbell test article.

One such device that was produced was in the form of a dumbbell 0.35 inches in length with substantially disk-like termini 0.20 inches in diameter and 0.05 inches in thickness. The connection between the two disks had a substantially circular cross-section, 0.062 inches in diameter. FIG. 5 provides engineering drawings of this dumbbell device. This design was injection molded using a 85/15 lactide/glycolide copolymer as a control and a polymer blend of the present invention, specifically a melt blend of 10 weight percent bimodal poly(p-dioxanone) and 90 weight percent 85/15 (mole basis) bimodal lactide/glycolide copolymer. The poly (p-dioxanone) is made up of 90 weight percent of a resin having a weight average molecular weight of 80,000 Daltons and 10 weight percent of a resin having a weight average molecular weight of 10,000 Daltons. Likewise, 85/15 lactide/glycolide copolymer is made up of 90 weight percent of a resin having a weight average molecular weight of 90,000 Daltons and 10 weight percent of a resin having a weight average molecular weight of 10,000 Daltons. It should be noted that this blend composition falls outside the ranges of pending U.S. patent application Ser. No. 12/887,995.

The articles, so produced, were thermally annealed without restraint at 60, 70, and 80° C. for 8, 4 and 4 hours, respectively. The devices molded from the 85/15 lactide/glycolide copolymer showed substantial shrinkage and warpage after this annealing process. The devices molded from the inventive blend were substantially free of shrinkage and warpage after annealing.

A further embodiment of the present inventive blends has a first absorbable polymer type that is a polylactide polymer or a copolymer of lactide and glycolide and a second absorbable polymer type that is poly(p-dioxanone), wherein the first absorbable polymer type or the second absorbable polymer type or the first absorbable polymer type and the second absorbable polymer type comprise a first polymeric component and a second polymeric component. The first polymeric component has a higher weight average molecular weight than the second polymeric component and at least one of the components is at least partially end-capped by a carboxylic acid. The novel polymeric blends are useful for manufacturing medical devices having dimensional stability, having engineered degradation and breaking strength retention in vivo.

In a preferred embodiment of the invention the injection molded part is visible in the surgical field because the polymeric blend has a violet colorant, or dye, interspersed throughout. This dye, D&C Violet No. 2, is introduced to the blend as part of the poly(p-dioxanone) homopolymer. Alternatively, colorant may be introduced to the blend as part of the lactide-based polymer. In yet another variation, the dye may be added at the time the polymer components are blended together, such as during a melt blending or dry blending process. It will be evident to one skilled in the art that the colorants may be added to the polymer compositions of the present invention in a variety of conventional manners in addition to the approaches described above. The colorants may include D&C Violet No. 2 and D&C Blue No. 6, at sufficiently effective amounts, for example ranging from about 0.01 weight percent to about 0.3 weight percent of the polymer blend or medical device. For surgical applications where color is not needed or desirable, undyed poly(p-dioxanone) homopolymer is used in the blend, so that the surgical article has no color.

The absorbable medical devices of the present invention that are made from the polymer blends of the present invention include but are not limited to conventional medical devices, especially implantable medical devices, including staples, tacks, clips, sutures, tissue fixation devices, mesh fixation devices, anastomosis devices, suture and bone anchors, tissue and bone screws, bone plates, prostheses, support structures, tissue augmentation devices, tissue ligating devices, patches, substrates, meshes, tissue engineering scaffolds, drug delivery devices, and stents, and the like and equivalents.

EXAMPLES

The following examples are illustrative of the principles and practice of the present invention, although not limited thereto. While the following examples demonstrate certain embodiments of the invention, they are not to be interpreted as limiting the scope of the invention, but rather as contributing to a complete description of the invention.

Example 1

Synthesis of 85/15 Poly(L(−)-Lactide-Co-Glycolide): Polymer of Normal Molecular Weight Distribution Into a suitable conventional 15-gallon stainless steel, oil jacketed reactor equipped with agitation, 43.778 kg of L(−)-lactide and 6.222 kg of glycolide were added along with 121.07 g of dodecanol and 9.02 mL of a 0.33M solution of stannous octoate in toluene. The reactor was closed and a purging cycle, along with agitation at a rotational speed of 12 RPM in an upward direction, was initiated. The reactor was evacuated to pressures less than 200 mTorr followed by the introduction of nitrogen gas to a pressure slightly in excess of one atmosphere. The cycle was repeated several times to ensure a dry atmosphere.

At the end of the final introduction of nitrogen, the pressure was adjusted to be slightly above one atmosphere. The vessel was heated at a rate of 180° C. per hour until the oil temperature reached approximately 130° C. The vessel was held at 130° C. until the monomer was completely melted and the batch temperature reached 110° C. At this point the agitation rotation was switched to the downward direction. When the batch temperature reached 120° C., the agitator speed was reduced to 7.5 RPM, and the vessel was heated using an oil temperature of approximately 185° C., with a heat up rate of approximately 60° C. per hour, until the molten mass reached 180° C. The oil temperature was maintained at approximately 185° C. for a period of 2.5 hours.

At the end of the reaction period, the agitator speed was reduced to 5 RPM, the oil temperature was increased to 190° C., and the polymer was discharged from the vessel into suitable containers for subsequent annealing. The containers were introduced into a nitrogen annealing oven set at 105° C. for a period of approximately 6 hours; during this step the nitrogen flow into the oven was maintained to reduce degradation due to moisture.

Once this annealing cycle was complete, the polymer containers were removed from the oven and allowed to cool to room temperature. The now crystallized polymer was removed from the containers, bagged, and placed into a freezer set at approximately −20° C. for a minimum of 24 hours. The polymer was removed from the freezer and placed into a conventional Cumberland granulator fitted with a sizing screen to produce polymer granules of approximately 3/16 inches in size. The granules were then sieved to remove any "fines" and then weighed. The net weight of the ground polymer was 39.46 kg, which was then placed into a conventional 3 cubic foot Patterson-Kelley tumble dryer.

The dryer was closed and the pressure is reduced to less than 200 mTorr. Once the pressure was below 200 mTorr, tumbler rotation was activated at a rotational speed of 8-15 RPM and the batch was vacuum conditioned for a period of 10 hours. After the 10 hour vacuum conditioning, the oil temperature was set to a temperature of 120° C., for a period of 32 hours. At the end of this heating period, the batch was allowed to cool for a period of at least 4 hours, while maintaining rotation and high vacuum. The polymer was discharged from the dryer by pressurizing the vessel with nitrogen, opening the slide-gate, and allowing the polymer granules to descend into waiting vessels for long term storage.

The long term storage vessels were air tight and outfitted with valves allowing for evacuation so that the resin was stored under vacuum. The resin was characterized. It exhibited an inherent viscosity of 1.79 dL/g, as measured in hexafluoroisopropanol at 25° C. at a concentration of 0.10 g/dL. Differential Scanning Calorimetry (DSC) using the heating rate of 10° C./min revealed a glass transition temperature of 59° C. and a melting transition of 150° C., with a heat of fusion about 35 J/g. Nuclear magnetic resonance (NMR) analysis confirmed that the resin was a random copolymer of polymerized L(-)-lactide and glycolide, with a composition of about 85 percent polymerized L(-)-lactide and about 15 percent polymerized glycolide on a molar basis.

Example 2

Synthesis of 85/15 Poly(L(-)-Lactide-Co-Glycolide): Lower Molecular Weight Polymer Into a suitable conventional 2-gallon stainless steel, oil jacketed reactor equipped with agitation, 5.253 kg of L(-)-lactide and 0.747 kg of glycolide were added along with 48.43 g of dodecanol and 1.08 mL of a 0.33M solution of stannous octoate in toluene. The reactor was closed and a purging cycle, along with agitation at a rotational speed of 25 RPM in an upward direction, was initiated. The reactor was evacuated to pressures less than 200 mTorr followed by the introduction of nitrogen gas to a pressure slightly in excess of one atmosphere. The cycle was repeated several times to ensure a dry atmosphere.

At the end of the final introduction of nitrogen, the pressure was adjusted to be slightly above one atmosphere. The vessel was heated at a rate of 180° C. per hour until the oil temperature reached approximately 130° C. The vessel was held at 130° C. until the monomer was completely melted and the batch temperature reached 110° C. At this point the agitation rotation was switched to the downward direction. When the batch temperature reached 120° C., the agitator speed was reduced to 20 RPM, and the vessel was heated using an oil temperature of approximately 185° C., with a heat up rate of approximately 60° C. per hour, until the molten mass reached 180° C. The oil temperature was maintained at approximately 185° C. for a period of 2.5 hours.

At the end of the reaction period, the agitator speed was reduced to 4 RPM, the oil temperature was increased to 190° C., and the polymer was discharged from the vessel into suitable containers (aluminum pie plates) for subsequent annealing. The annealing, drying, and grinding procedures were conducted using the same approach as described earlier in Example 1.

The resulting dried copolymer 85/15 poly(L(-)-lactide-co-glycolide) resin had a glass transition temperature of 54° C., a melting point of 152° C., and an enthalpy of fusion of 42 J/g, as measured by DSC using a heating rate of 10° C./min. The resin had a weight average molecular weight of 41,000 Daltons, and exhibited an inherent viscosity of 0.83 dL/g, as measured in hexafluoroisopropanol at 25° C. at a concentration of 0.10 g/dL. Nuclear magnetic resonance analysis confirmed that the resin was a random copolymer of polymerized L(-)-lactide and glycolide, with a composition of about 85 percent polymerized L(-)-lactide and about 15 percent polymerized glycolide on a molar basis.

Example 3

Synthesis of Poly(p-Dioxanone): Standard Molecular Weight Polymer

Into a suitable conventional 65-gallon stainless steel, oil-jacketed reactor equipped with agitation, 164.211 kg of p-dioxanone monomer (PDO) was added along with 509 grams of dodecanol, 164 grams of D&C Violet No. 2 Dye, and 100 grams of a 0.33M solution of stannous octoate in toluene. The reactor was closed and a purging cycle, along with agitation at a rotational speed of 12 RPM in an upward direction, was initiated. The reactor was evacuated to pressures less than 500 mTorr followed by the introduction of nitrogen gas. The cycle was repeated several times to ensure a dry atmosphere.

At the end of the final introduction of nitrogen, the pressure was adjusted to be slightly above one atmosphere. The vessel was heated at a rate of 180° C. per hour until the oil temperature reached approximately 100° C. The oil temperature was held at 100° C. until the batch temperature reached 50° C., at which point the agitator rotation was changed to the downward direction. When the batch temperature reached 90° C., the oil temperature was reset to 95° C. These conditions were maintained, and samples were taken from the vessel to be measured for Brookfield viscosity. When the polymer batch viscosity reached at least 110 centipoise, the batch was ready for discharge. The agitator speed was reduced to 5 RPM, and a pre-heated filter was attached to the vessel discharge port. The polymer was discharged from the vessel into suitable containers, under a nitrogen purge, covered, and transferred into a nitrogen curing oven set at 80° C. A solid state polymerization was initiated for a period of approximately 96 hours; during this step the nitrogen flow into the oven was maintained to minimize degradation due to moisture.

Once the solid state curing cycle was complete, the polymer containers were removed from the oven and allowed to cool to room temperature. The crystallized polymer was removed from the containers, and placed into a freezer set at approximately -20° C. for a minimum of 24 hours. The polymer was removed from the freezer and ground in a conventional Cumberland granulator fitted with a sizing screen to reduce the polymer granules to approximately 3/16 inches in size. The granules were then sieved to remove any "fines" and then placed into a conventional 20 cubic foot Patterson-Kelley tumble dryer.

The dryer was closed and the pressure was reduced to less than 2 mmHg. Once the pressure was below 2 mmHg, dryer rotation was activated at a rotational speed of 6 RPM with no heat for 10 hours. After the 10 hour vacuum period, the oil temperature was set to 95° C. at a heat up rate of 120° C. per hour. The oil temperature was maintained at 95° C. for a period of 32 hours. At the end of this heating period, the batch was allowed to cool for a period of at least 4 hours, while maintaining rotation and vacuum. The polymer was discharged from the dryer by pressurizing the vessel with nitrogen, opening the discharge valve, and allowing the polymer granules to descend into waiting vessels for long term storage. The storage vessels were air tight and outfitted with valves allowing for evacuation so that the resin was stored under vacuum.

The resin was characterized. It exhibited an inherent viscosity of 1.90 dL/g, as measured in hexafluoroisopropanol at 25° C. and at a concentration of 0.10 g/dL. Differential Scanning Calorimetry using a heating rate of 10° C./min revealed a glass transition temperature of about -8° C. (minus eight degrees Celsius), a melting transition at about 114° C., with a heat of fusion of about 88 J/g. Nuclear magnetic resonance analysis confirmed that the resin was the homopolymer poly (p-dioxanone), with a residual monomer content less than 2 percent.

Example 4

A) Preparation of Bimodal Molecular Weight Poly(p-Dioxanone)

Bimodal molecular weight polymer blends were prepared according the procedures described elsewhere (U.S. Pat. No.

8,236,904 B2). It will be described in Example 4 herein the preparation of a new inventive blend composition based on the 85/15 Lac/Gly copolymer of Example 1 and a poly(p-dioxanone) bimodal molecular weight blend.

The poly(p-dioxanone) bimodal molecular weight blend contained 70 weight percent of a poly(p-dioxanone) having a weight average molecular weight of 80,000 Daltons and a 30 weight percent of a poly(p-dioxanone) polymer having a weight average molecular weight of 24,000 Daltons. Calorimetric (DSC) data on this 70/30 poly(p-dioxanone) bimodal molecular weight blend in a form of dried pellets revealed a glass transition temperature of −5° C., melting point of 107° C., with a heat of fusion of 62 J/g, which corresponds to a crystallinity level of about 50 percent. Under both non-isothermal and isothermal quiescent conditions, the poly(p-dioxanone) blend crystallized much faster than either of the individual unimodal poly(p-dioxanone) components of standard and lower molecular weight, respectively.

B) Dry Blending of a Unimodal Lactide/Glycolide Copolymer with Bimodal Molecular Weight Poly(p-Dioxanone) Blend Appropriate amounts of the 85/15 lactide/glycolide copolymer and the poly(p-dioxanone) bimodal molecular weight polymer components, in divided form (ground), were combined in dry blends. These dry blends are produced on a weight basis, depending on the particular application and surgical need. In the present example, the bimodal molecular weight poly(p-dioxanone) polymer described in Example 4A at 20 weight percent, and a lactide/glycolide copolymer described in Example 1 at 80 weight percent, were dry blended as described directly below.

Into a clean, conventional 3-cubic foot Patterson-Kelley dryer, 4.0 kg of granules of the 85/15 lactide/glycolide copolymer of Example 1 and 1.0 kg of pellets 70/30 poly(p-dioxanone) bimodal molecular weight blend of Example 4A were added. The dryer was closed, and the vessel pressure was reduced to less than 200 MTorr. The rotation was started at 7.5 RPM and continued for a minimum period of one hour. The dry blend was then discharged into portable vacuum storage containers, and these containers were placed under vacuum, until ready for the melt blending step.

C) Melt Blending of a Unimodal Lactide/Glycolide Copolymer with Bimodal Molecular Weight Poly(p-Dioxanone) Blend Once the dry blends had been produced and had been vacuum conditioned for at least three days, the melt-blending step was begun. A conventional ZSK-30 twin-screw extruder was fitted with screws designed for melt blending utilizing dual vacuum ports for purposes of volatilizing residual monomer. The screw design contained several different types of elements, including conveying, compression, mixing and sealing elements. The extruder was fitted with a three-hole die plate, and a chilled water bath with water temperature set between 40° F. and 70° F. was placed near the extruder outlet. A strand pelletizer and pellet classifier were placed at the end of the water bath. The extruder temperature zones were heated to a temperature of 160° C. to 180° C., and the vacuum cold traps were set to −20° C. The pre-conditioned dry blend granules were removed from vacuum and placed in a twin-screw feed hopper under nitrogen purge. The extruder screws were set to a speed of 175-225 RPM, and the feeder was turned on, allowing the dry blend to be fed into the extruder.

The polymer melt blend was allowed to purge through the extruder until the feed was consistent, at which point the vacuum was applied to the two vacuum ports. The polymer blend extrudate strands were fed through the water bath and into the strand pelletizer. The pelletizer cut the strands into appropriate sized pellets; it was found that pellets with a diameter of 1 mm and an approximate length of 3 mm sufficed. The pellets were then fed into the classifier. The classifier separated substantially oversized and undersized pellets from the desired size, usually a weight of about 10-15 mg per pellet. This process continued until the entire polymer dry blend was melt blended in the extruder, and formed into substantially uniform pellets. Samples were taken throughout the extrusion process and were measured for polymer characteristics such as inherent viscosity, molecular weight and composition. Once the melt-blending process was completed, the pelletized polymer was placed in polyethylene bags, weighed, and stored in a freezer below −20° C. to await devolatilization of residual monomer.

The polymer melt-blend was placed into a conventional 3-cubic foot Patterson-Kelley dryer, which was placed under vacuum. The dryer was closed and the pressure was reduced to less than 200 mTorr. Once the pressure was below 200 mTorr, dryer rotation was activated at a rotational speed of 10 RPM with no heat for 6 hours. After the 6 hour period, the oil temperature was set to 85° C. at a heat up rate of 120° C. per hour. The oil temperature was maintained at 85° C. for a period of 12 hours. At the end of this heating period, the batch was allowed to cool for a period of at least 4 hours, while maintaining rotation and vacuum. The polymer melt-blend pellets were discharged from the dryer by pressurizing the vessel with nitrogen, opening the discharge valve, and allowing the polymer pellets to descend into waiting vessels for long term storage. The storage vessels were air tight and outfitted with valves allowing for evacuation so that the inventive resin blend of the present invention could be stored under vacuum.

The inventive resin blend was characterized. The resultant 20 weight percent poly(p-dioxanone), 80 weight percent lactide/glycolide copolymer melt blend composition exhibited a melt flow index of 0.113 g/10 min, as measured at 190° C. with the standard weight of 6,600 grams. Differential scanning calorimetry revealed a glass transition temperature of about 58° C., and two melting transition temperatures at about 106 and 148° C. The heat of fusion calculated during the first heat (heating rate 10° C./min) was 27.2 J/g.

Example 5

Dry Blending of Bimodal Molecular Weight Lactide/Glycolide Blends with Unimodal Poly(p-Dioxanone) Homopolymer In the present example, a series of bimodal molecular weight lactide/glycolide compositions were dried blend with the poly(p-dioxanone) homopolymer described in Example 3 following the procedures of Example 4, with the exception that the bimodal component was the L/G copolymer, not the poly(p-dioxanone) component. The dry blends were made with a unimodal, standard molecular weight poly(p-dioxanone) component at a final blend concentration of 2.5, 5.0, 7.5, 10, and 20 weight percent.

Example 6

Melt Blending of Bimodal Molecular Weight Lactide/Glycolide Blends with Unimodal Poly(p-Dioxanone) Homopolymer Following the method described above in Example 4C, melt blends of various compositions comprising lactide/glycolide bimodal molecular weight blends and unimodal poly(p-dioxanone) homopolymer were also produced. The polymers and melt-blends outlined below in Table 2 were produced using these methods.

TABLE 2

Melt Blends of Bimodal Molecular Weight 85/15 Lac/Gly Compositions with Unimodal Poly(p-dioxanone) Homopolymer (PDS)

| Blend ID | Weight percent of Example 1 in 85/15 Lac/Gly blend | Weight percent of Example 2 in 85/15 Lac/Gly blend | PDS weight percent in the final blend | Melt Index* (g/10 min) |
|---|---|---|---|---|
| 6A | 75 | 25 | 20 | 0.175 |
| 6B | 75 | 25 | 10 | 0.147 |

TABLE 2-continued

Melt Blends of Bimodal Molecular Weight 85/15 Lac/Gly Compositions with Unimodal Poly(p-dioxanone) Homopolymer (PDS)

| Blend ID | Weight percent of Example 1 in 85/15 Lac/Gly blend | Weight percent of Example 2 in 85/15 Lac/Gly blend | PDS weight percent in the final blend | Melt Index* (g/10 min) |
|---|---|---|---|---|
| 6C | 75 | 25 | 5 | 0.156 |
| 6D | 75 | 25 | 2.5 | 0.139 |
| 6E | 75 | 25 | 0 | 0.162 |

*Melt Index measurements (MT987 Extrusion Plastometer, Tinius Olsen, Willow Grove, PA, USA) were conducted at 190° C. using 6,600 g weight disc. The die diameter was 0.0260 inches, while the die length was 0.315 inches.

Example 7

Crystallization Kinetics Evaluation of Inventive Blends Compositions

Differential Scanning Calorimetry (DSC) was used to investigate the crystallization kinetics of the inventive blend compositions. The following methods/conditions were used:

a) First heat measurements—a 5 to 8 milligram sample of interest was quenched to −60° C. [minus 60 degrees Celsius] in a DSC pan equipped with nitrogen purge, followed by the constant heating rate scan of 10° C./min b) Second heat measurements—the sample of interest after melting in a DSC pan at 185° C., and followed by a rapid quench (−60° C./min) to −60° C. was then heated at the constant heating rate of 5° C./min to 185° C.

A summary of DSC results obtained on pellets of a control and blends of the present invention is shown in Table 3 below. The pellets underwent elevated temperature devolatilization sufficient to develop a nearly maximum level of crystallinity. This is reflected in the "first heat" results. The "second heat" results reflect the inherent crystallization properties of the test samples because the thermal history would have been erased, as is well known.

TABLE 3

DSC Calorimetric Properties of Control and Inventive Dried Bimodal Blends

| Blend ID | Comments | First Heat Data (10° C./min) | | | Second Heat Data (5° C./min) | | |
|---|---|---|---|---|---|---|---|
| | | $T_g$ (° C.) | $T_m$ (° C.) | $\Delta H_m$ (J/g) | $T_g$ (° C.) | $T_m$ (° C.) | $\Delta H_m$ (J/g) |
| 7A | 80 wt. % standard 85/15 Lac/Gly with 20% of Unimodal Poly(p-dioxanone), PDS (control, non-inventive sample) | 55.8 | 148 | 26.1 | 55.2 | 151 | 1.0 |
| 7B | 80 wt. % standard 85/15 Lac/Gly with 20% of Bimodal PDS, Example 4C | 58.1 | 148 | 27.2 | 55.1 | 150 | 4.5 |
| 7C | 100 wt. % bimodal 85/15 Lac/Gly (75/25 high/lower Mw wt. %) AKA 6E | 57.1 | 147 | 35.5 | 55.3 | 149 | 15.5 |
| 7D | 97.5 wt. % bimodal 85/15 Lac/Gly with 2.5% of PDS AKA 6D | 57.6 | 149 | 30.0 | 55.4 | 150 | 9.5 |
| 7E | 95 wt. % bimodal 85/15 Lac/Gly with 5% of PDS AKA 6C | 58.6 | 150 | 30.4 | 55.8 | 149 | 13.7 |
| 7F | 90 wt. % bimodal 85/15 Lac/Gly with 10% of PDS AKA 6B | 58.2 | 149 | 29.2 | 55.0 | 151 | 3.3 |
| 7G | 80 wt. % bimodal 85/15 Lac/Gly with 20% of PDS AKA 6A | 58.6 | 149 | 28.6 | 55.5 | 151 | 9.0 |
| 7I | 95 wt. % bimodal 85/15 Lac/Gly with 5% of bimodal PDS | 55.4 | 150 | 30.3 | 55.2 | 148 | 19.1 |

It should be noted that that the second heat $\Delta H_m$ values (the last column of Table 3) indicate faster crystallization of the inventive blends over the control [Standard 85/15 Lac/Gly with 20% of PDS homopolymer, Sample 7A]. That is, $\Delta H_m$ values for the inventive blends ranged from 3.3 to 19.1 J/g versus only 1.0 J/g for the control, Sample 7A.

Additionally, when the samples of the inventive blends and the control were subjected to nearly optimal thermal processing conditions, thereby allowing the respective resins to crystallize to their highest practical levels, the inventive blends achieved slightly higher crystallinity levels than the control as evident from the $\Delta H_m$ values obtained from the first heat measurements (5$^{th}$ column of Table 3).

Surprisingly, it was observed that the presence of bimodal PDS part in the inventive blend 7B (Example 4C) promoted the crystallization of difficult-to-crystallize 85/15 Lac/Gly copolymer, as shown by the second heat DSC data in Table 3. To be clear, Sample 7B, made from a blend of standard [unimodal molecular weight distribution] 85/15 Lac/Gly with 20 weight percent of a bimodal poly(p-dioxanone), had a $\Delta H_m$ of 4.5 J/g as compared to a value of 1.0 J/g for the Sample 7A control. Surprisingly, the vast majority of 4.5 J/g melting endotherm originated from difficult-to-crystallize 85/15 L/G part. The control, Sample 7A was standard [unimodal] 85/15 Lac/Gly copolymer blended with 20 weight percent unimodal poly(p-dioxanone).

The correlation of the rate of crystallization of the inventive blends with the dimensional stability of molded parts was verified experimentally; data is provided further along in this application.

Example 8A

Injection Molding of Control Polymers and Blends, and Inventive Bimodal Blends into Straps and Dumbbells Injection molding is a process well known in the plastics industry. It is designed to produce parts of various shapes and sizes by melting a plastic resin, mixing, and then injecting the molten resin into a suitably shaped mold. For the purpose of this invention, two injection molding shapes were explored: straps and dumbbells. These shapes are shown in FIGS. 1 and 5, respectively. After the resin is solidified, the part is generally ejected from the mold and the process continued. For the purposes of this invention, a conventional 30-ton electrically controlled injection molding machine was used. The polymers and blends of Examples 1, 4, and 6 were processed by the injection molding machine in the following general manner.

The polymer was fed by gravity from a hopper, under nitrogen purge, into a heated barrel and allowed to melt. The polymer was moved forward in the barrel by a screw-type plunger, eventually into a heated chamber in front of the screw at the distal end of the barrel. The screw was then advanced forward in a translational motion, which forced the molten polymer through a nozzle that sat against the mold, allowing the polymer to enter a specially designed mold cavity, through a gate and runner system. The polymer was formed into the part in the mold cavity, and allowed to cool at a given temperature for a period of time. The part was then removed from the mold, or ejected, and separated from the runner.

The injection molding cycle consisted of the entire series of events during the process. It began when the mold closed, and was followed by the injection of the molten polymer into the mold cavity. Once the cavity was filled, hold pressure was maintained to compensate for material shrinkage. Next, the screw-plunger turned and retracted, feeding the next "shot" to the front of the screw. While preparing the next shot in the barrel, the part in the mold was cooled to sufficient temperature, and the mold opened and the part was ejected. The next cycle initiated upon the closing of the mold. The cycle times ranged from about 25 seconds to about 75 seconds and were based on a number of factors, including part size and material composition.

Example 8B

Annealing Molded Parts

Once the articles of Example 8A were injection molded, they were then subjected to an annealing cycle to mature the polymer morphology. The articles in Example 8A were annealed using an annealing fixture that supported the parts from distortion within the horizontal plane of the part. Although this annealing fixture is intended to aid in the resistance of distortion at elevated temperatures during annealing, it will not prevent dimensionally unstable parts from warping. The annealing cycle used for the articles in Example 8A was composed of three steps: 60° C. for 8 hours, 70° C. for 4 hours, and then 80° C. for 4 hours. The purpose of the 60° C. step is to further crystallize the poly(p-dioxanone) phase in the blend before reaching the crystallization temperatures for the poly(lactide-co-glycolide) phase. The 70° C. step begins to crystallize the poly(lactide-co-glycolide) phase before reaching the last step in the cycle. Finally, the 80° C. step further crystallizes the poly(lactide-co-glycolide) phase. It should be noted that for a given device and given composition annealing conditions may be found that optimize certain important performance characteristics. These advantageous annealing conditions can be developed through experimentation, changing the annealing temperature and annealing duration, and measuring the response.

Once the injection parts of Example 8A were annealed, they were identified as the annealed parts of Example 8B.

Example 9

Calorimetric Properties of Annealed Dumbbells

Calorimetric data was obtained utilizing Differential Scanning Calorimetry (DSC) [at a heating rate of 10° C./min with a sample weight of 5 to 8 mg] on a number of annealed dumbbells. These include samples based on the neat 85/15 L/G copolymer of Example 1 having a normal molecular weight distribution [Sample DB 9B]; a control blend of 80 weight percent 85/15 L/G copolymer of normal molecular weight distribution and 20 weight percent PDS also of normal molecular weight distribution [DB 9A]; the inventive blend of the present invention of 80 weight percent 85/15 L/G copolymer of normal molecular weight distribution and 20 weight percent PDS of bimodal molecular weight distribution [DB 9C]; and, the inventive blends of the present invention ranging in composition of 80 to 97.5 weight percent 85/15 L/G copolymer of bimodal molecular weight distribution and 2.5 to 20 weight percent PDS of normal molecular weight distribution [Samples DB 9D, DB 9E, DB 9F, DB 9G, respectively]. The DSC results are summarized in Table 4 below.

TABLE 4

Calorimetric (DSC) Properties of Control Annealed[1] Dumbbells and Corresponding DSC Calorimetric Properties of Control and Inventive Dumbbells Made from Bimodal Blends

| Dumbbell Sample ID | Comments | DSC First Heat Data (10° C./min) | | | |
|---|---|---|---|---|---|
| | | $T_g$ [PDS] (° C.) | $T_g$ [Lactide-Based Copolymer] (° C.) | $T_m$ (° C.) | $\Delta H_m$ (J/g) |
| DB 9A | Middle-Cut Section of Annealed Dumbbell Molded From Control From Prior Art, a Blend of 80% 85/15 L/G + 20% PDS | −19.6 | 46.3 | 102/147 | 28.9 |

TABLE 4-continued

Calorimetric (DSC) Properties of Control Annealed[1] Dumbbells and Corresponding DSC Calorimetric Properties of Control and Inventive Dumbbells Made from Bimodal Blends

| Dumbbell Sample ID | Comments | DSC First Heat Data (10° C./min) | | | |
|---|---|---|---|---|---|
| | | $T_g$ [PDS] (° C.) | $T_g$ [Lactide-Based Copolymer] (° C.) | $T_m$ (° C.) | $\Delta H_m$ (J/g) |
| DB 9B | Middle-Cut Section of Annealed Dumbbell Molded From 85/15 L/G Copolymer of Example 1 (Unimodal Molecular Weight Distribution) | NA | 53.5 | 148 | 26.5 |
| DB 9C | Middle-Cut Section of Annealed Dumbbell Molded From the Blend of Example 4C 80% (Unimodal) 85/15 L/G + 20% Bimodal PDS | −10.8 | 53.5 | 105/147 | 37.3 |
| DB 9D | Middle-Cut Section of Annealed Dumbbell Molded From the Blend of Example 6A 80% Bimodal 85/15 L/G + 20% (Unimodal) PDS | −8.3 | 56.3 | 105/148 | 38.3 |
| DB 9E | Middle-Cut Section of Annealed Dumbbell Molded From the Blend of Example 6B 90% Bimodal 85/15 L/G + 10% (Unimodal) PDS | −14.6 | 55.3 | 105/149 | 31.2 |
| DB 9F | Middle-Cut Section of Annealed Dumbbell Molded From the Blend of Example 6C 95% Bimodal 85/15 L/G + 5% (Unimodal) PDS | −13.5 | 56.1 | 106/150 | 29.0 |
| DB 9G | Middle-Cut Section of Annealed Dumbbell Molded From the Blend of Example 6D 97.5% Bimodal 85/15 L/G + 2.5% (Unimodal) PDS | −14.7 | 56.2 | 102/149 | 29.2 |

[1]Annealing conditions: 60° C. (8 hrs) followed by 70° C. (4 hrs) followed by 80° C. (4 hrs)

The DSC results shown in Table 4 above allow for a number of conclusions. The glass transition temperature of PDS was identified in those blends containing this component. This is indicative of a phase-separated morphology. The melting behavior resulted in the observation of two melting transition temperatures, $T_{m1}$ and $T_{m2}$, although overlapping, in those articles based on blends of 85/15 L/G copolymer and PDS. One of these melting transitions temperatures corresponded to PDS and one corresponded to the L/G copolymer. The PDS-based melting endotherms ranged from 102° C. to 106° C., while the L/G-based melting ranged from 147° C. to 150° C., further indicative of the phase separated morphology. Due to the overlapping nature of the melting endotherms, the combined heat of melting, $\Delta H_m$, is reported in the last column of Table 4. It is well established that that the heat of fusion is proportional to the crystallinity level of the part. We can thus model the crystallinity level by following the $\Delta H_m$.

It is noted that all the annealed molded articles prepared from the resins based on blends of L/G copolymer and PDS listed in Table 4 exhibited higher $\Delta H_m$ values when compared to the L/G copolymer alone [Sample DB 9B]. These higher $\Delta H_m$ values indicate an expected higher crystallinity levels.

Unexpectedly, it was found that the inventive blend of 80 weight percent 85/15 L/G copolymer of normal molecular weight distribution and 20 weight percent PDS of bimodal molecular weight distribution, Sample DB 9C, exhibited a $\Delta H_m$ value much higher than that exhibited by the normally distributed control of Sample DB 9A.

The Sample DB 9D, based on the inventive blend 80 weight percent 85/15 L/G copolymer of bimodal molecular weight distribution 20 weight percent PDS of normal molecular weight distribution also unexpectedly exhibited a $\Delta H_m$ value much higher than that exhibited by the normally distributed control of Sample DB 9A. This demonstrates that when either of the blend components possesses a bimodal molecular weight distribution, a higher $\Delta H_m$ value is observed. The importance of higher $\Delta H_m$ values is related to the numerous advantages of possessing higher crystallinity values. These include higher mechanical properties such as higher stiffness and strength, as well as better dimensional stability of formed articles.

Attention is now drawn to the results obtained on samples containing lower levels of PDS blend component, Samples DB 9D, DB 9E, DB 9F, and DB 9G. Each of these blends was made with an 85/15 L/G copolymer having a bimodal molecular weight distribution. That is, $\Delta H_m$ values of 38.3, 31.2, 29.0, and 29.2 J/g were obtained with PDS blend component levels of 20, 10, 5, and 2.5 weight percent, respectively. These values were all higher than that observed for the neat 85/15 alone [Sample DB 9B]; even samples with as low as 2.5 weight percent PDS blend component [Sample DB 9G] exhibited a $\Delta H_m$ value comparable to the control blend containing 20 weight percent PDS [Sample DB 9A], when the former is based on the inventive bimodal composition of the present invention. It is quite unexpected that a blend containing only 2.5 weight percent PDS would have a comparable $\Delta H_m$ value as a blend containing 20 weight percent PDS. There are advantages to minimizing the amount of PDS in a blend. These include producing articles that are stiffer and that are stronger; the mechanical strength retention post-implantation of articles prepared therefrom would also be extended with lower levels of PDS blend component.

Example 10

Tensile Properties of Annealed Dumbbells Made from a Control Blend and a Series of Inventive Bimodal Blend Compositions Annealed test specimens in the form of dumbbells made by injection molding as described in Example 8A and 8B (specifically Samples DB 9A, DB 9C, DB 9D, DB 9E, DB 9F, and DB 9G) were examined with respect to mechanical properties.

The annealed dumbbells were tested utilizing a conventional mechanical tester, Instron Model 5544 (Norwood, Mass., USA), using a 100 lbs. load cell. All instruments were within calibration at the time of testing. The specimens were loaded in tension at a rate of 0.5 in/min until fracture. The maximum force was recorded as the tensile strength of the specimen. The Young's Modulus was calculated as the slope of the line linking two points located on the linear region of the force-extension curve of the test specimen. The following formula was utilized:

$$E=(\Delta F/A_0)/(\Delta L/L_0)$$

where E is the calculated Young's Modulus, $\Delta F$ is the change in force measured at the selected points, $A_0$ is the initial cross-sectional area of the specimen, $\Delta L$ is the change in cross-head displacement at selected points and $L_0$ is the gage length of the specimen. The initial cross-sectional area and the gage length considered in the calculations were $2.83 \times 10^{-3}$ in$^2$ and 0.25 inches, respectively. The summary of data is given in Table 5.

The data of Table 5 above also show that with decreasing PDS content, the dumbbells made from the inventive bimodal blends of the present invention are increasingly stronger and stiffer. It was found that the level of PDS cannot be lowered without limit, however, if dimensional stability of a medical article is an important requirement.

Example 11

Dimensional Stability

The molded articles of Example 8A and 8B [that is molded articles before and after annealing] in the form of straps (AKA tacks or staples; see FIGS. 1 and 2) were tested for dimensional stability. The dimensions of the molded articles were measured prior to annealing and after annealing; additionally photographic images were taken [see FIG. 6 to FIG. 9]. Although it is not expected to have dimensions match exactly, it is clear that unacceptable levels of distortion exist. In some cases, excessive distortion results in diminished functionality.

The test articles of Example 8A and 8B in the form of straps are geometrically complex and have a number of critical dimensions. For instance, if the legs of the molded article distort excessively, the ability of the device to penetrate and hold tissue will be reduced. Likewise, if the barbs of the molded article were to shrink significantly, functionality would be reduced because of diminished ability to hold tissue. Every design will have its own critical dimensions. It is believed that the design of the straps of Examples 8A and 8B is representative of a challenging device regarding dimensional stability; this is felt in part because of geometric complexity. Specifically, the fine part size will tend to increase

TABLE 5

Tensile Strength and Young's Modulus (Stiffness) Data for selected Dumbbell samples Made from Bimodal blends of the Present Invention and a control

| Sample ID | Comments | Max. Load (lbf) | Max. Load SDEV | Young's Modulus (kpsi) | YM SDEV |
|---|---|---|---|---|---|
| DB 9A | Control From Prior Art, Based on a blend of 80 Wt. % (Unimodal) 85/15 L/G Copolymer + 20 Wt. % (Unimodal) PDS | 26.30 | 1.68 | 130.3 | 4.81 |
| DB 9C | Based on the Blend of Example 4C 80 Wt. % (Unimodal) 85/15 L/G + 20 Wt. % Bimodal PDS | 27.73 | 1.09 | 132.1 | 3.06 |
| DB 9D | Based on the Blend of Example 6A 80 Wt. % Bimodal 85/15 L/G + 20 Wt. % (Unimodal) PDS | 28.83 | 0.94 | 130.8 | 3.94 |
| DB 9E | Based on the Blend of Example 6B 90 Wt. % Bimodal 85/15 L/G + 10 Wt. % (Unimodal) PDS | 28.73 | 0.41 | 140.8 | 4.57 |
| DB 9F | Based on the Blend of Example 6C 95 Wt. % Bimodal 85/15 L/G + 5 Wt. % (Unimodal) PDS | 30.33 | 0.53 | 141.9 | 4.83 |
| DB 9G | Based on the Blend of Example 6D 97.5 Wt. % Bimodal 85/15 L/G + 2.5 Wt. % (Unimodal) PDS | 31.65 | 0.62 | 144.8 | 4.98 |

The data of Table 5 above show that for the same amount of PDS (20%), annealed dumbbells made from bimodal blends are stronger and stiffer than the control blend made with the same overall composition, but with unimodal polymers. This may be due to higher crystallinity levels of annealed dumbbells made from the inventive bimodal blends as evident from Table 4 (Samples DB 9C and 9D).

molecular orientation during injection molding leading to an increased driving force for distortion of the ejected part [that is the part after removal from the mold cavity] at elevated temperatures as seen in annealing, and/or sterilization, and/or storage. Parts were evaluated and characterized in a "pass/fail" manner. Disposition of the molded articles was based on gross warping effects, of which an article is considered to have passed if excessive distortion is not evident. Likewise, if excessive distortion is evident, the part is said to have failed. Inherently, all injection molded articles have some degree of residual stress after molding, so parts that display tolerable levels of distortion are said to have passed the dimensional stability test. For the articles of Examples 8A and 8B, the tip-to-tip distance is a critical dimension; see FIG. 1.

Examples 8A and 8B were also considered critical dimensions. A barb length of less than or equal to 0.136 inches were considered unacceptable and denoted as "failure mode 2" or "fm2". The photographic images and dimensions were captured using a Keyence digital microscope, model VHX-600, with a magnification of 20×. A summary of the test results are shown in Table 6 below.

TABLE 6

Calorimetric (DSC) Properties of Annealed[1] Control Straps and Corresponding Straps Made from Blends with at Least One Polymeric Component Possessing a Bimodal Molecular Weight Distribution.

| | | First Heat Data (10° C./min) | | | | |
|---|---|---|---|---|---|---|
| EXAMPLE | Comments | $T_g$ [PDS Based] (° C.) | $T_g$ [L/G Copolymer Based] (° C.) | $T_m^{(2)}$ (° C.) | $\Delta H_m$ (J/g) | Dimensionally Stable |
| Straps Based on a Lactide/Glycolide Copolymer ONLY (Unimodal) - Example 1 | | | | | | |
| STR 11-1 | Unimodal 85/15 L/G Copolymer (Control 1) | Molded parts failed to hold shape, sticking issues and distortions were observed | | | | |
| Straps Based on Blends in Which the Blend Components are of a Unimodal Nature: | | | | | | |
| STR 11-2 | Prior Art Blend of 80% Unimodal 85/15 L/G Copolymer and 20% Unimodal PDS (Control 2) | −9.8 | 52.6 | 103/ 148 | 33.6 | YES |
| Straps Based on Blends in Which the Lactide-Based Blend Component is of a Bimodal Nature: | | | | | | |
| STR 11-3 | Prepared from Blend 6D 97.5% Bimodal 85/15 L/G Copolymer and 2.5% Unimodal PDS | −11.9 | 57.5 | 102/ 148 | 28.9 | NO |
| STR 11-4 | Prepared from Blend 6C 95% Bimodal 85/15 L/G Copolymer and 5% Unimodal PDS | −12.0 | 57.9 | 103/ 149 | 29.0 | NO |
| STR 11-5 | Prepared from Blend 6B 90% Bimodal 85/15 L/G Copolymer and 10% Unimodal PDS | −10.1 | 57.2 | 105/ 146 | 32.1 | YES |
| Straps Based on Blends in Which the Poly(p-dioxanone) Blend Component is of a Bimodal Nature: | | | | | | |
| STR 11-6 | Prepared from Blend 4C 95% Unimodal 85/15 L/G Copolymer and 5% Bimodal PDS | −12.7 | 55.6 | 102/ 147 | 27.1 | NO |
| STR 11-7 | Prepared from Blend 4C 90% Unimodal 85/15 L/G Copolymer and 10% Bimodal PDS | −11.8 | 54.8 | 104/ 147 | 28.5 | NO |
| STR 11-8 | Prepared from Blend 4C 80% Unimodal 85/15 L/G Copolymer and 20% Bimodal PDS | −8.2 | 54.4 | 105/ 146 | 35.4 | YES |

[1]Analysis conducted on the crown portion of an annealed molded strap. The annealing conditions employed were 60° C. for 8 hours followed by 70° C. for 4 hours followed by 80° C. for 4 hours.
[2]Listed herein are two values; the first is represents the melting point of PDS-based blend component, $T_{m1}$, and the second value represents the melting point observed for the lactide-based blend component, $T_{m2}$.

FIG. 2 is a drawing of the device of FIG. 1 showing the critical dimensions of said device. These dimensions, if changed by lack of dimensional stability, can lead to poor performance and or failure of the device. A tip-to-tip distance of less than 0.115 inches for the strap articles of Example 8A and 8B were said to be acceptable, while a tip-to-top distance greater than or equal to 0.115 inches were said to be unacceptable and denoted as "failure mode one" or "fm1". Likewise, the length of the barb members from the straps of In Table 6 above, the calorimetric properties of annealed straps of Example 8B are provided along with the results of dimensional stability testing. The calorimetric data was a result of DSC (first heat) testing as described earlier in this application. The "first heat" DSC measurements were used to calculate the heats of fusion, $\Delta H_m$ (J/g), of the annealed straps [see Example 8B]. These values are directly proportional to the relative crystallinity level present in the test articles.

The articles shown in Table 6 are annealed straps based on blends in which the blend components are of a unimodal nature, [STR 11-1]; annealed straps based on a lactide/glycolide copolymer of Example 1 only, a unimodal copolymer, [STR 11-2]; and two groups of annealed straps test articles based on bimodal blend components. In one case, the annealed straps were based on blends in which the lactide-based blend component is of a bimodal nature; the level of the minor blend component, poly(p-dioxanone), was 2.5, 5 or 10 weight percent. In the other case, the annealed straps were based on blends in which the poly(p-dioxanone) blend component was of a bimodal nature; the level of the minor blend component, bimodal poly(p-dioxanone), was 5, 10 or 20 weight percent.

An examination of the strap articles of Example STR 11-1, which are based on an 85/15 lactide/glycolide (unimodal) copolymer the strap articles of Example STR 11-1 acted as a control group—Control 1) revealed that although the articles exhibited crystallinity after annealing, the molded parts failed to hold shape during this process; they were dimensionally unstable with significant distortions being observed.

The injection molded straps of Example STR 11-2 were based on the prior art blend of 80% (unimodal) 85/15 L/G copolymer and 20% (unimodal) PDS and represent a second control group—Control 2. As expected, these articles exhibited dimensional stability. Dimensional stability is provided by the presence of 20 weight percent of (unimodal) poly(p-dioxanone). The annealed straps of Example STR 11-2 exhibited a $\Delta H_m$ of 33.6 J/g, indicative of a significant level of crystallinity. The presence of the (unimodal) poly(p-dioxanone) blend component does however decrease the stiffness of the article; minimizing the amount of poly(p-dioxanone) present in the blend would lead to stiffer articles which in certain applications would be advantageous. To achieve dimensional stability in finely detailed molded articles, however, it has been shown that a minimum of about 12.4 weight percent of poly(p-dioxanone) is required.

The injection molded straps of Examples STR 11-3 to STR 11-5 are based on blends in which the lactide-based blend component is of a bimodal nature. Specifically, these were made from bimodal 85/15 L/G copolymer blended with unimodal PDS, in which the latter polymer is present at 2.5, 5, and 10 weight percent, respectively. The articles of Example STR 11-5 exhibited dimensional stability; this corresponds to PDS being present at the 10 weight percent level. Based on the crystallization data of Table 4 summarizing results obtained on annealed injection molded dumbbells, articles based on the blend of 80% bimodal 85/15 L/G copolymer and 20% PDS are expected to be dimensionally stable. Note that the $\Delta H_m$ values for (a) a neat unimodal 85/15 L/G copolymer, (b) a blend based on 80% unimodal 85/15 L/G copolymer and 20% unimodal PDS, and (c) a blend based on 80% bimodal 85/15 L/G copolymer and 20% unimodal PDS were 26.5, 28.9, and 38.3 J/g, respectively. Clearly, substituting a bimodal 85/15 L/G copolymer blend component for the unimodal 85/15 L/G copolymer blend component resulted in a very large increase in $\Delta H_m$, 9.4 J/g, a 32 percent increase. Note that the annealed strap of Example STR 11-5 was made with only 10 weight percent (unimodal) PDS, yet exhibited a $\Delta H_m$ of 32.1 J/g close to the 33.6 value exhibited by Control 2, Example STR 11-2, made with twice the amount of (unimodal) PDS blend component, 20 percent.

The annealed injection molded straps of Examples STR 11-6 to STR 11-8 were based on straps derived from blends in which the poly(p-dioxanone) blend component was of a bimodal nature. Specifically, these were made from unimodal 85/15 L/G copolymer blended with bimodal PDS, in which the latter polymer was present at 5, 10, and 20 weight percent, respectively. The articles of Example STR 11-8 exhibited dimensional stability; this corresponds to PDS being present at the 20 weight percent level. The $\Delta H_m$ of this example 35.4 J/g, was above the value exhibited by the control article Example STR 11-2, 33.6 J/g. The corresponding straps made with 5 and 10 weight percent bimodal PDS did not exhibit dimensional stability as noted in Table 6; in both of these cases, the level of crystallinity was lower as evidenced by the lower $\Delta H_m$ values: 27.1 and 28.5 J/g, respectively. Dimensional stability was found to be dependent on the $\Delta H_m$ (or crystallinity) of the article; when the annealed article exhibited a $\Delta H_m$ of greater than about 30 J/g, the article tended to be dimensionally stable.

Figure 6:
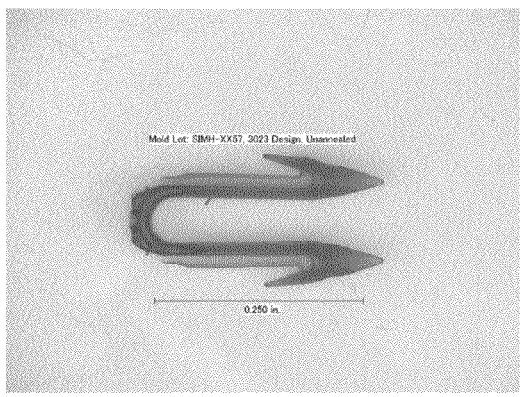
FIG. 6 is a photograph of an injection molded tack of Sample STR 11-7 prior to annealing made from the polymer composition of Example 4C having 10 weight percent poly (p-dioxanone).
Figure 7:
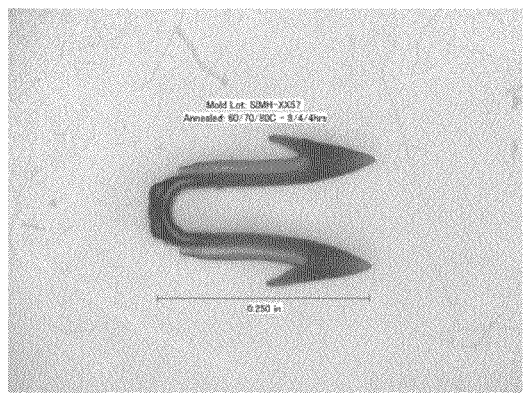
FIG. 7 is a photograph of an injection molded tack of Sample STR 11-7 after annealing made from the polymer composition of Example 4C having 10 weight percent poly (p-dioxanone), said injection molded tacks exhibiting unacceptable warping after annealing.

Further evidence of dimensional stability or instability is presented in the photographs of FIG. 6 to FIG. 9 where the injection molded straps made from the polymer composition of Example 4C having 10 or 20 weight percent poly(p-dioxanone) blend component are depicted. FIG. 6 is a photograph of an injection molded tack of Sample STR 11-7 prior to annealing made from the polymer composition of Example 4C having 10 weight percent poly(p-dioxanone); and, FIG. 7 is a photograph of an injection molded tack of Sample STR 11-7 after annealing made from the polymer composition of Example 4C having 10 weight percent poly(p-dioxanone), said injection molded tacks exhibiting unacceptable warping after annealing.

Figure 8:
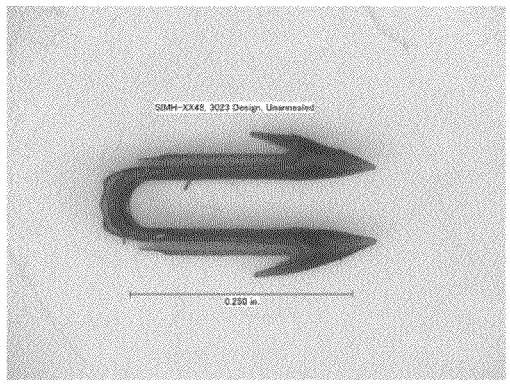
FIG. 8 is a photograph of an injection molded tack of Sample STR 11-8 prior to annealing made from the polymer composition of Example 4C having 20 weight percent poly (p-dioxanone).
Figure 9:
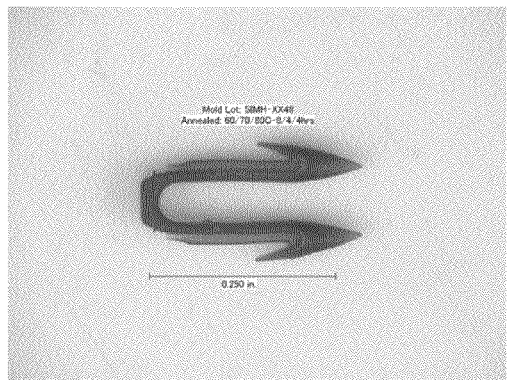
FIG. 9 is a photograph of an injection molded tack of Sample STR 11-8 after annealing made from the polymer composition of Example 4C having 20 weight percent poly (p-dioxanone), said injection molded tacks exhibiting superior dimensional stability and an acceptable level of warping after annealing.

FIG. 8 is a photograph of an injection molded tack of Sample STR 11-8 prior to annealing made from the polymer composition of Example 4C having 20 weight percent poly(p-dioxanone); FIG. 9 is a photograph of an injection molded tack of Sample STR 11-8 after annealing made from the polymer composition of Example 4C having 20 weight percent poly(p-dioxanone), said injection molded tacks exhibiting superior dimensional stability and an acceptable level of warping after annealing.

Returning to the data presented in Table 6, it can be seen that in the cases of the annealed straps of Examples 11-2 to 11-9, two separate glass transition phenomena and two separate melting endotherms were observed. These corresponded to the poly(p-dioxanone) [PDS] blend component and the lactide-based blend component. The observation of two glass transition temperatures is universally accepted as evidence of component immiscibility. All poly(p-dioxanone)-based glass transition temperatures were between about −8 C and about −13° C., while the glass transition temperatures associated with the lactide-rich-based blend component were between about 53° C. and about 58° C.

Two melting points were observed in the annealed injection molded articles made from the various blends shown in Table 6. The observation of two melting points is evidence that each blend component was semicrystalline in nature. All poly(p-dioxanone)-based melting temperatures were between 102° C. and 105° C., while the melting temperatures associated with the lactide-rich-based blend component were observed to be between 146 and 149° C.

It is felt that the inventive concepts of this application might be practiced in a variety of ways. Further examples of practice are provided below. Examples 12 through 14 support three categories of practice, Case I, Case II and Case III.

Case I refers to situations in which the first absorbable polymer type is made up of a mixture of a lactide-rich L/G copolymer of higher molecular weight and a lactide-rich L/G copolymer of lower molecular weight. It is noted that a mixture of higher and lower molecular weight crystallizable polylactide homopolymers might be used for this first absorbable polymer type as described elsewhere in this application. In Case I, the second absorbable polymer type is unimodal poly (p-dioxanone).

Case II refers to situations in which the first absorbable polymer type is made up of a unimodal lactide-rich L/G copolymer (or crystallizable polylactide homopolymer) and the second absorbable polymer type is made up of a mixture of higher and lower molecular weight poly(p-dioxanone).

Case III refers to situations in which the first absorbable polymer type is made up of a mixture of a lactide-rich L/G copolymer (or crystallizable polylactide homopolymer) of higher molecular weight and a lactide-rich L/G copolymer of lower molecular weight, and the second absorbable polymer type is made up of a mixture of higher and lower molecular weight poly(p-dioxanone).

The embodiments described herein can be summarized in Table 7 below:

TABLE 7

| | Lactide-Rich L/G Copolymer | | Poly(p-di-oxanone), PDS | | PDS Blend Wt. % and Wt. % of Each Component[1] |
|---|---|---|---|---|---|
| Case | $M_{w1}$ (g/mol) | $M_{w2}$ (g/mol) | $M_{w1}$ (g/mol) | $M_{w2}$ (g/mol) | |
| I | 80,000 | 30,000 | 72,000 | / | 20% [(64 + 16) + (20 + 0)] |
| II | 82,000 | / | 75,000 | 25,000 | 18% [(82 + 0) + (14 + 4)] |
| III | 90,000 | 10,000 | 85,000 | 10,000 | 14% [(77.4 + 8.6) + (12.6 + 1.4)] |

[1][(Higher MW L/G + Lower MW L/G) + (Higher MW PDS + Lower MW PDS)]

Case I (the Lactide/Glycolide Copolymer Component Possesses a Bimodal Molecular Weight Distribution)

It is to be understood that a mixture of a lactide/glycolide copolymer and a lower molecular weight lactide/glycolide copolymer may be substituted for the lactide/glycolide copolymer blend component. Of particular utility are those lactide/glycolide copolymer mixtures differing in their weight average molecular weight by a factor of two or more. Additionally, the weight average molecular weight of the lower molecular weight lactide/glycolide copolymer component must be at least 10,000 Daltons. It is to be understood that of particular advantage is when the lower molecular weight lactide/glycolide copolymer component represents between 5 and 40 weight percent of the total lactide/glycolide copolymer present in the inventive blend.

The following examples are illustrative of the principles and practice of the present invention, although not limited thereto. While the following examples demonstrate certain embodiments of the invention, they are not to be interpreted as limiting the scope of the invention, but rather as contributing to a complete description of the invention.

Example 12

Case I (the Poly(Lactide-Co-Glycolide) Component Possesses a Bimodal Molecular Weight Distribution Sixty-four kilograms of pellets or ground material of a lactide/glycolide copolymer having a weight average molecular weight of 80,000 Daltons is dry mixed with 16 kilograms of pellets or ground material of a lactide/glycolide copolymer having a weight average molecular weight of 30,000 Daltons. This mixture is compounded to result in a bimodal blend of lactide/glycolide copolymer. This blend is further compounded with poly(p-dioxanone) having a weight average molecular weight of approximately 72,000 Daltons so that the poly(p-dioxanone) represents about 20 weight percent of the final blend.

Alternately, one could have conducted a single melt compounding in which the feed stock was based on 64 kilograms of a lactide/glycolide copolymer having a weight average molecular weight of 80,000 Daltons, 16 kilograms a lactide/glycolide copolymer having a weight average molecular weight of 30,000 Daltons, and 20 kilograms poly(p-dioxanone) having a weight average molecular weight of approximately 72,000 Daltons. Thus the amount of poly(p-dioxanone) represents about 20 weight percent of the final blend, and the lactide/glycolide copolymer is made with a bimodal blend in which the ratio molecular weight of the higher molecular weight lactide/glycolide copolymer to the molecular weight of the lower molecular weight lactide/glycolide copolymer is (64/16=) four.

It should be clear to one having ordinary skill in the art that similar blends differing in composition can be made in like manner.

Case II (the Poly(p-Dioxanone) Component Possesses a Bimodal Molecular Weight Distribution)

It is further understood that a mixture of a poly(p-dioxanone) and a lower molecular weight poly(p-dioxanone) may be substituted for the poly(p-dioxanone). Of particular utility are those poly(p-dioxanone) mixtures differing in their weight average molecular weight by a factor of two or more. Additionally, the weight average molecular weight of the lower molecular weight poly(p-dioxanone) component must be at least 10,000 Daltons. It is to be understood that of particular advantage is when the lower molecular weight poly(p-dioxanone) component represents between 5 and 40 weight percent of the total poly(p-dioxanone) present in the inventive blend.

Example 13

Case II (the Poly(p-Dioxanone) Component Possesses a Bimodal Molecular Weight Distribution Fourteen kilograms of pellets or ground material of poly (p-dioxanone) having a weight average molecular weight of 75,000 Daltons is dry mixed with four kilograms of pellets or ground material of poly(p-dioxanone) having a weight average molecular weight of 25,000 Daltons. This mixture is compounded to result in a bimodal blend of poly(p-dioxanone). This blend is further compounded with a lactide/glycolide copolymer having a weight average molecular weight of 82,000 Daltons so that the poly(p-dioxanone) represents about 18 weight percent of the final blend.

Alternately, one could have conducted a single melt compounding in which the feed stock was based on 82 kilograms of a lactide/glycolide copolymer having a weight average molecular weight of 82,000 Daltons, 14 kilograms of poly(p-dioxanone) having a weight average molecular weight of 75,000 Daltons, and 4 kilograms poly(p-dioxanone) having a weight average molecular weight of approximately 25,000 Daltons.

It should be clear to one having ordinary skill in the art that similar blends differing in composition can be made in like manner.

Case III (Both Components Possess Bimodal Molecular Weight Distributions)

It is to be understood that a mixture of a lactide/glycolide copolymer and a lower molecular weight lactide/glycolide copolymer may be substituted for the lactide/glycolide copolymer blend component and that a mixture of a poly(p-dioxanone) and a lower molecular weight poly(p-dioxanone) may be substituted for the poly(p-dioxanone). Of particular utility are those lactide/glycolide copolymer mixtures differing in their weight average molecular weight by a factor of two or more. Additionally, the weight average molecular weight of the lower molecular weight lactide/glycolide copolymer component must be at least 10,000 Daltons. It is to be understood that of particular advantage is when the lower molecular weight lactide/glycolide copolymer component represents between 5 and 40 weight percent of the total lactide/glycolide copolymer present in the inventive blend. Likewise, of particular utility are those poly(p-dioxanone) mixtures differing in their weight average molecular weight by a factor of two or more. Additionally, the weight average molecular weight of the lower molecular weight poly(p-dioxanone) component must be at least 10,000 Daltons. It is to be understood that of particular advantage is when the lower molecular weight poly(p-dioxanone) component represents between 5 and 40 weight percent of the total poly(p-dioxanone) present in the inventive blend.

Example 14

Case III (Both Components Possess Bimodal Molecular Weight Distributions)

A total of 77.4 kilograms of pellets or ground material of a lactide/glycolide copolymer having a weight average molecular weight of 90,000 Daltons is dry mixed with 8.6 kilograms of pellets or ground material of a lactide/glycolide copolymer having a weight average molecular weight of 10,000 Daltons. This mixture is compounded to result in a bimodal blend of lactide/glycolide copolymer. A total of 12.6 kilograms of pellets or ground material of poly(p-dioxanone) having a weight average molecular weight of 85,000 Daltons is dry mixed with 1.4 kilograms of pellets or ground material of poly(p-dioxanone) having a weight average molecular weight of 10,000 Daltons. This mixture is compounded to result in a bimodal blend of poly(p-dioxanone).

These two blends are further compounded together so that the (bimodal) poly(p-dioxanone) represents about 14 weight percent of the final blend.

Alternately, a single melt compounding is conducted in which the feed stock is based on 77.4 kilograms of a lactide/glycolide copolymer having a weight average molecular weight of 90,000 Daltons, 8.6 kilograms a lactide/glycolide copolymer having a weight average molecular weight of 10,000 Daltons, and 12.6 kilograms poly(p-dioxanone) having a weight average molecular weight of approximately 85,000 Daltons, 1.4 kilograms poly(p-dioxanone) having a weight average molecular weight of approximately 10,000 Daltons. Thus, the amount of (bimodal) poly(p-dioxanone) represents about 14 weight percent of the final blend, and the (bimodal) lactide/glycolide copolymer represents about 86 weight percent of the final blend.

The ratio molecular weight of the higher molecular weight lactide/glycolide copolymer to the molecular weight of the lower molecular weight lactide/glycolide copolymer is (77.4/8.6=) nine and the ratio of the molecular weight of the higher molecular weight poly(p-dioxanone) polymer to the molecular weight of the lower molecular weight poly(p-dioxanone) polymer is (12.6/1.4=) nine.

It should be clear to one having ordinary skill in the art that similar blends differing in composition can be made in like manner.

The novel polymer blends of the present invention having a bimodal molecular weight distribution have many advantages. The advantages are numerous and include the following. An increased the rate of crystallization of the absorbable resin will aid the development of dimensional stability in molded parts.

An increase in the rate of crystallization of the absorbable resin can lower the cycle time needed during injection molding to form appropriate parts. This faster production rate provides economic advantage. The increase in the rate of crystallization of the absorbable resin can lower the cycle time during injection molding to form molded parts, decreasing the residence time of the resin in the barrel thus avoiding unwanted thermal degradation. This is expected to result in higher molecular weight parts with higher performance characteristics; the minimization of the degradation during molding also results in more robust manufacturing processes.

With the expected higher crystallinity levels achieved in the molded parts, part stiffness may be increased.

It is to be noted that with the expected faster crystallization rates, and the development of higher percent crystallinity being achieved in molded parts, it is possible to shift the composition of the blend to lower poly(p-dioxanone) levels. With the reduction of the low $T_g$ polymer component, poly (p-dioxanone), stiffness is further increased.

The novel polymer blends are suitable for making implantable medical devices that still possesses good dimensional stability in molded parts that have higher moduli than previously available absorbable blends by virtue of increasing the crystallization rate, and the overall crystallinity developed in the molded part.

Providing blend components possessing bimodal molecular weight distributions enables the preferred inventive blends to degrade faster post-implantation than the corresponding blends made with blend components based on unimodal molecular weight polymers, while adequately stabilizing the molded part so as to undergo processing to avoid warping and dimensional instability during further in-house processing, sterilization, packaging, transportation, storage.

Example 15

Calculating the Minimum Weight Percent of Bimodal Poly(p-Dioxanone) in the Invention when the Lactide-Rich Polymer has a Unimodal Molecular Weight Distribution As stated previously, the minimum level of poly(p-dioxanone) was dependent on the molar amount of polymerized lactide present in the lactide-based polymer present in the blend. In the case of the lactide-based polymer possessing a unimodal molecular weight distribution and the poly(p-dioxanone) possessing a bimodal molecular weight distribution, the weight percent of the bimodal poly(p-dioxanone) can be calculated using the equation found below.

$$\text{Weight Percent Bimodal Poly(p-dioxanone)} = (215.6212/\text{Mol Percent Polymerized Lactide})^{2.7027} - 1.177$$

For example, when the composition of the unimodal lactide-co-glycolide copolymer was 82/8 (on a mol basis), the minimum weight percent of bimodal poly(p-dioxanone) in the blend was calculated to be 12.5 percent and the maximum amount was 50. Likewise, if the composition of the unimodal lactide-co-glycolide copolymer was 86/14 (on a mol basis), the minimum weight percent of bimodal poly(p-dioxanone) in the blend was calculated to be 10.8 percent and the maximum amount was 50. Table 8 contains a chart of the range of bimodal poly(p-dioxanone), expressed as minimum and maximum weight percent, in the blend of the subject invention.

TABLE 8

Inventive Blend Compositions of Unimodal Lactide-Rich, Lactide/Glycolide (Co)Polymer with Bimodal Poly(p-Dioxanone)

| Mol Percent of Polymerized Lactide in the Unimodal Lactide-Based (Co)Polymer | Minimum Weight Percent Bimodal Poly(p-dioxanone) Polymer in the Blend | Maximum Weight Percent Bimodal Poly(p-dioxanone) Polymer in the Blend |
|---|---|---|
| 100 | 6.8 | 50 |
| 99 | 7.0 | 50 |
| 98 | 7.2 | 50 |
| 97 | 7.5 | 50 |
| 96 | 7.7 | 50 |
| 95 | 8.0 | 50 |
| 94 | 8.2 | 50 |
| 93 | 8.5 | 50 |
| 92 | 8.8 | 50 |
| 91 | 9.1 | 50 |
| 90 | 9.4 | 50 |
| 89 | 9.7 | 50 |
| 88 | 10.1 | 50 |
| 87 | 10.4 | 50 |
| 86 | 10.8 | 50 |
| 85 | 11.2 | 50 |
| 84 | 11.6 | 50 |
| 83 | 12.0 | 50 |
| 82 | 12.5 | 50 |
| 81 | 12.9 | 50 |
| 80 | 13.4 | 50 |
| 79 | 13.9 | 50 |
| 78 | 14.4 | 50 |
| 77 | 15.0 | 50 |
| 76 | 15.6 | 50 |
| 75 | 16.2 | 50 |
| 74 | 16.8 | 50 |
| 73 | 17.5 | 50 |
| 72 | 18.2 | 50 |
| 71 | 18.9 | 50 |
| 70 | 19.7 | 50 |

Example 16

Calculating the Minimum Weight Percent of Unimodal or Bimodal Poly(p-Dioxanone) in the Invention when the Lactide-Rich Polymer has a Bimodal Molecular Weight Distribution In the case of the lactide-based polymer possessing a bimodal molecular weight distribution and the poly(p-dioxanone) possessing either a unimodal or a bimodal molecular weight distribution, the weight percent of the poly(p-dioxanone) can be calculated using the equation found below.

Weight Percent Poly(p-dioxanone)=$(215.6212/\text{Mol Percent Polymerized Lactide})^{2.7027} - 4.877$ Wherein the Lactide-Based Polymer Possesses a Bimodal Molecular Weight Distribution For example, when the composition of the bimodal lactide-co-glycolide copolymer was 82/8 (on a mol basis), the minimum weight percent of unimodal or bimodal poly(p-dioxanone) in the blend was calculated to be 8.8 percent and the maximum amount was 50. Likewise, if the composition of the bimodal lactide-co-glycolide copolymer was 86/14 (on a mol basis), the minimum weight percent of unimodal or bimodal poly(p-dioxanone) in the blend was calculated to be 7.1 percent and the maximum amount was 50. Table 9 contains a chart of the range of poly(p-dioxanone), expressed as minimum and maximum weight percent, in the blend of the subject invention. It should be noted that the poly(p-dioxanone) in this case may be a unimodal polymer or a bimodal polymer.

TABLE 9

Inventive Blend Compositions of Bimodal Lactide-Rich, Lactide/Glycolide (Co)Polymer with Unimodal or Bimodal Poly(p-Dioxanone)

| Mol Percent of Polymerized Lactide in the Bimodal Lactide-Based (Co)Polymer | Minimum Weight Percent Poly(p-dioxanone) Polymer in the Blend | Maximum Weight Percent Poly(p-dioxanone) Polymer in the Blend |
|---|---|---|
| 100 | 3.1 | 50 |
| 99 | 3.3 | 50 |
| 98 | 3.5 | 50 |
| 97 | 3.8 | 50 |
| 96 | 4.0 | 50 |
| 95 | 4.3 | 50 |
| 94 | 4.6 | 50 |
| 93 | 4.8 | 50 |
| 92 | 5.1 | 50 |
| 91 | 5.4 | 50 |
| 90 | 5.7 | 50 |
| 89 | 6.1 | 50 |
| 88 | 6.4 | 50 |
| 87 | 6.7 | 50 |
| 86 | 7.1 | 50 |
| 85 | 7.5 | 50 |
| 84 | 7.9 | 50 |
| 83 | 8.3 | 50 |
| 82 | 8.8 | 50 |
| 81 | 9.2 | 50 |
| 80 | 9.7 | 50 |
| 79 | 10.2 | 50 |
| 78 | 10.7 | 50 |
| 77 | 11.3 | 50 |
| 76 | 11.9 | 50 |
| 75 | 12.5 | 50 |
| 74 | 13.1 | 50 |
| 73 | 13.8 | 50 |
| 72 | 14.5 | 50 |
| 71 | 15.3 | 50 |
| 70 | 16.0 | 50 |

Although this invention has been shown and described with respect to detailed embodiments thereof, it will be understood by those skilled in the art that various changes in form and detail thereof may be made without departing from the spirit and scope of the claimed invention.

We claim:
1. An absorbable polymer blend, comprising:
a first absorbable polymer comprising at least 50 weight percent of a lactide-rich polymer comprising about 100 mole percent to about 70 mole percent polymerized lactide and about 0 mole percent to about 30 mole percent polymerized glycolide; and,
a second absorbable polymer comprising poly(p-dioxanone),
wherein the maximum weight percent of poly(p-dioxanone) in the blend is 50 weight percent and the minimum weight percent of poly(p-dioxanone) in the blend is sufficient so that the polymer blend effectively provides dimensional stability to a manufactured article, and further wherein one or both of the first absorbable polymer and the second absorbable polymer are bimodal molecular weight distribution polymers each bimodal molecular weight distribution polymer comprising a blend of:

(a) from about 60 to 95 wt. % of a first component polymer having a first weight average molecular weight between about 50,000 to about 500,000 Daltons; and (b) from about 5 to 40 wt. % of a second component polymer having a second weight average molecular weight between about 10,000 to about 50,000 Daltons, the weight average molecular weight ratio of said first molecular weight to said second molecular weight is at least about two to one.

2. The blend of claim 1, wherein the first polymer comprises a polymer selected from the group consisting of poly(L(−)-lactide), poly(D(+)-lactide), poly(L(−)-lactide)/poly(D(+)-lactide) stereocomplex, and a lactide-rich lactide/glycolide copolymer.

3. The absorbable polymer blend of claim 1 wherein at least one of the first or second polymers additionally comprises acid-capped end groups.

4. The absorbable polymer blend of claim 1, wherein the first absorbable polymer is a bimodal molecular weight distribution polymer.

5. The absorbable polymer blend of claim 4, wherein the second absorbable polymer is a unimodal molecular weight distribution polymer.

6. The blend of claim 4, wherein the first polymer comprises a first amount of a polylactide or lactide-rich lactide/glycolide copolymer having first a weight average molecular weight between about 50,000 to about 500,000 Daltons; and a second amount of a polylactide or lactide-rich lactide/glycolide copolymer having a second weight average molecular weight between about 10,000 to about 50,000 Daltons, the weight average molecular weight ratio of the first molecular weight distribution to the second molecular weight distribution is at least about two to one; wherein a substantially homogeneous blend of the first and second amounts of the absorbable polymer is formed in a ratio of between about 60/40 to 95/5 Weight/Weight percent.

7. The absorbable polymer blend of claim 1, wherein the first absorbable polymer is a unimodal molecular weight distribution polymer.

8. The blend of claim 7, wherein the first polymer comprises a polymer selected from the group consisting of poly(L(−)-lactide), poly(D(+)-lactide), poly(L(−)-lactide)/poly(D(+)-lactide) stereocomplex, and a lactide-rich lactide/glycolide copolymer, said blend having a first weight average molecular weight between about 50,000 to about 500,000 Daltons.

9. The absorbable polymer blend of claim 7, wherein the second absorbable polymer is a bimodal molecular weight distribution polymer.

10. The blend of claim 9, wherein the second polymer comprises a first amount of a poly(p-dioxanone) polymer having a first weight average molecular weight between about 50,000 to about 500,000 Daltons; and a second amount of a poly(p-dioxanone) polymer having a second weight average molecular weight between about 10,000 to about 50,000 Daltons, wherein the weight average molecular weight ratio of the first molecular weight distribution to the second molecular weight distribution is at least about two to one, and a substantially homogeneous blend of the first and second amounts of the absorbable polymer is formed in a ratio of between about 60/40 to 95/5 Weight/Weight percent.

11. The absorbable polymer blend of claim 1, wherein the first and second polymers each are bimodal molecular weight distribution polymers.

12. The blend of claim 11, wherein the first polymer comprises a first amount of a polylactide or lactide-rich lactide/glycolide copolymer having first a weight average molecular weight between about 50,000 to about 500,000 Daltons; and a second amount of a polylactide or lactide-rich lactide/glycolide copolymer having a second weight average molecular weight between about 10,000 to about 50,000 Daltons, the weight average molecular weight ratio of the first molecular weight distribution to the second molecular weight distribution is at least about two to one; wherein a substantially homogeneous blend of the first and second amounts of the absorbable polymer is formed in a ratio of between about 60/40 to 95/5 Weight/Weight percent, and wherein the second polymer comprises a first amount of a poly(p-dioxanone) polymer having a first weight average molecular weight between about 50,000 to about 500,000 Daltons; and a second amount of a poly(p-dioxanone) polymer having a second weight average molecular weight between about 10,000 to about 50,000 Daltons, wherein the weight average molecular weight ratio of the first molecular weight distribution to the second molecular weight distribution is at least about two to one, and a substantially homogeneous blend of the first and second amounts of the absorbable polymer is formed in a ratio of between about 60/40 to 95/5 Weight/Weight percent.

13. An absorbable polymer blend, comprising:
a first absorbable polymer comprising at least 50 weight percent of a lactide-rich polymer comprising about 100 mole percent to about 70 mole percent polymerized lactide and about 0 mole percent to about 30 mole percent polymerized glycolide; and,
a second absorbable polymer comprising poly(p-dioxanone),
wherein the maximum weight percent of poly(p-dioxanone) in the blend is 50 weight percent and the minimum weight percent of poly(p-dioxanone) in the blend is sufficient so that the polymer blend effectively provides dimensional stability to a manufactured article, and further wherein one or both of the first absorbable polymer and the second absorbable polymer are bimodal molecular weight distribution polymers each bimodal molecular weight distribution polymer comprising a blend of:
(a) from about 60 to 95 wt. % of a first component polymer having a first weight average molecular weight between about 50,000 to about 500,000 Daltons; and
(b) from about 5 to 40 wt. % of a second component polymer having a second weight average molecular weight between about 10,000 to about 50,000 Daltons, the weight average molecular weight ratio of said first molecular weight to said second molecular weight is at least about two to one,
wherein further the minimum weight percent of poly(p-dioxanone) in the blend depends upon the molar amount of polymerized lactide in the lactide-rich polymer and is calculated by the expression:

Weight Percent Poly(p-dioxanone)=$(215.6212/\text{Mole Percent Polymerized Lactide})^{2.7027}-1.177$ when the lactide-rich polymer has a unimodal molecular weight distribution and the poly(p-dioxanone) has a bimodal molecular weight distribution and wherein the polymer blend provides dimensional stability to a manufactured article.

14. An absorbable polymer blend, comprising:
a first absorbable polymer comprising at least 50 weight percent of a lactide-rich polymer comprising about 100 mole percent to about 70 mole percent polymerized lactide and about 0 mole percent to about 30 mole percent polymerized glycolide; and,
a second absorbable polymer comprising poly(p-dioxanone), wherein the maximum weight percent of poly(p-dioxanone) in the blend is 50 weight percent and the minimum weight percent of poly(p-dioxanone) in the blend is sufficient so that the polymer blend effectively provides dimensional stability to a manufactured article, and further wherein one or both of the first absorbable polymer and the second absorbable polymer are bimodal molecular weight distribution polymers each bimodal molecular weight distribution polymer comprising a blend of:

(a) from about 60 to 95 wt. % of a first component polymer having a first weight average molecular weight between about 50,000 to about 500,000 Daltons; and (b) from about 5 to 40 wt. % of a second component polymer having a second weight average molecular weight between about 10,000 to about 50,000 Daltons, the weight average molecular weight ratio of said first molecular weight to said second molecular weight is at least about two to one, wherein the minimum weight percent of poly(p-dioxanone) in the blend depends upon the molar amount of polymerized lactide in the lactide-rich polymer and is calculated by the expression:

$$\text{Weight Percent Poly(p-dioxanone)} = (215.6212/\text{Mole Percent Polymerized Lactide})^{2.7027} - 4.877$$

when the lactide-rich polymer has a bimodal molecular weight distribution and the poly(p-dioxanone) has a unimodal or bimodal molecular weight distribution and wherein the polymer blend provides dimensional stability to a manufactured article.

15. A medical device comprising the absorbable polymer blend of claim 1.

16. A medical device comprising the absorbable polymer blend of claim 13.

17. A medical device comprising the absorbable polymer blend of claim 14.

18. A method of manufacturing a medical device, comprising the step of processing the absorbable polymer blend of claim 1 into a medical device.

19. A method of manufacturing a medical device, comprising the step of processing the absorbable polymer blend of claim 13 into a medical device.

20. A method of manufacturing a medical device, comprising the step of processing the absorbable polymer blend of claim 14 into a medical device.

21. The method of claim 18, wherein the method comprises melt processing.

22. The method of claim 19, wherein the method comprises melt processing.

23. The method of claim 20, wherein the method comprises melt processing.

* * * * *